United States Patent [19]

Ohnishi et al.

[11] Patent Number: 5,374,641

[45] Date of Patent: Dec. 20, 1994

[54] N-(3-PYRIDYLALKYL)SULFONAMIDE COMPOUNDS WHICH HAVE USEFUL PHARMACEUTICAL ACTIVITY

[75] Inventors: Hiroyuki Ohnishi, Kanagawa; Masazumi Miyakoshi, Tokyo; Masashi Isozaki, Kanagawa; Masayuki Fujitake, deceased, late of Kanagawa, by Junko Fujitake, legal representative; Naoya Mikami, Kanagawa; Ryohei Yanoshita, Kanagawa; Harue Akasofu, Kanagawa; Katsuyoshi Sugizaki, Kanagawa; Nobuyuki Nakata, Kanagawa, all of Japan

[73] Assignee: Terumo Kabushiki Kaisha, Tokyo, Japan

[21] Appl. No.: 840,165

[22] Filed: Feb. 24, 1992

[30] Foreign Application Priority Data

Feb. 25, 1991 [JP] Japan .................... 3-114154
Aug. 9, 1991 [JP] Japan .................... 3-200650
Aug. 9, 1991 [JP] Japan .................... 3-200651

[51] Int. Cl.[5] .................... C07D 213/42; H61K 31/44
[52] U.S. Cl. .................... 514/357; 546/338; 546/333
[58] Field of Search ............ 546/338, 333; 514/357

[56] References Cited

U.S. PATENT DOCUMENTS 4,610,981 9/1986 Marsico, Jr. et al. ............ 514/158
4,874,775 10/1989 Krumkalns et al. ............ 546/338

FOREIGN PATENT DOCUMENTS 0397044 11/1990 European Pat. Off. ......... 546/338
0405391A1 1/1991 European Pat. Off. ......... 546/338
3-227928 10/1991 Japan ...................... 546/338

OTHER PUBLICATIONS

Susan Budavari et al., "The Merck Index", 1989, Merch & Co., Inc., Rahway, N.J. 11th Ed.; Abstract 2807: Daltroban, p. 2807.

H. Onishi et al. "Pharmaceuticals Containing N-picolylsulfonamide derivatives for Prevention of Thrombosis"; Chemical Abstracts, vol. 116, No. 11, (1992), Abstract No. 99325H.

Primary Examiner—C. Warren Ivy
Assistant Examiner—Zinna N. Davis
Attorney, Agent, or Firm—Burns, Doane, Swecker & Mathis

[57] ABSTRACT

Illustrative examples of the N-(3-pyridylalkyl)sulfonamide derivative are represented by the following formulae [II] and [III]:

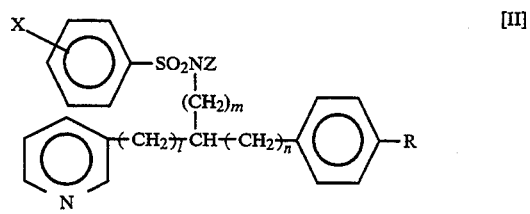

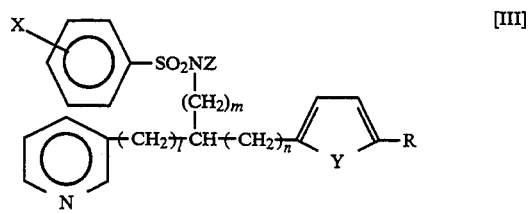

The derivatives are available for a thromboxane $A_2$ production inhibitor, a thromboxane $A_2$ antagonist, a prostaglandin $H_2$ antagonist, an anti-thrombus agent, a thrombus-preventing agent and an anti-allergy agent.

7 Claims, No Drawings

N-(3-PYRIDYLALKYL)SULFONAMIDE COMPOUNDS WHICH HAVE USEFUL PHARMACEUTICAL ACTIVITY

FIELD OF THE INVENTION

This invention relates to a novel N-(3-pyridylalkyl)-sulfonamide derivative and its pharmacologically acceptable salts and hydrates, and to pharmaceutical preparations containing thereof including a thromboxane $A_2$ production inhibitor, a thromboxane $A_2$ antagonist, a prostaglandin $H_2$ antagonist, an anti-thrombus agent, a thrombus-preventing agent and an anti-allergy agent.

BACKGROUND OF THE INVENTION

Great concern has been directed toward the development of anti-thrombus agents which can effectively prevent thrombosis-related diseases such as myocardial infarction, cerebral infarction and the like that are of frequent occurrence in recent years. It is known that thromboxane $A_2$ ($TXA_2$) which is a strong platelet coagulation factor produced from platelet and the like cells is taking an important role as a cause of these diseases, and that inhibition of its activity is an effective means for the prevention of thrombus formation.

Also, since $TXA_2$ and other chemical mediators such as leukotriene $D_4$ ($LTD_4$) are concerned in allergy, asthma and the like as smooth muscle contraction factors, inhibition of the $TXA_2$ activity is an effective means for the treatment of late asthma.

Taking such viewpoints into consideration, various $TXA_2$ synthesis inhibitors and $TXA_2$ antagonists have been developed, but each having each own problems. For example biosynthesis inhibitors such as Dazoxiben, Ozagrel and the like inhibit a thromboxane synthetase, which by contraries entails accumulation of this enzyme's substrate, prostaglandin $H_2$ ($PGH_2$). Similar to the case of $TXA_2$, $PGH_2$ itself and other prostaglandins derived from $PGH_2$, such as $PGE_2$, are possessed of platelet coagulation and smooth muscle contraction functions. In other words, in spite of the effect of these prior art inhibitors to inhibit $TXA_2$ production, the inhibition reaction generates coagulation- and contraction-causing substitutes which reduce actual drug effect by half. On the other hand, $TXA_2$ antagonists such as S-145, Daltroban and the like compete with the $TXA_2$ receptor which exists in platelets. Because of such a reaction mechanism, these antagonists exhibit effective $TXA_2$ inhibition activity by competing with the receptor when the amount of produced $TXA_2$ is small, but their efficacy decreases as the amount of produced $TXA_2$ increases. In such a case, therefore, it is necessary to inhibit $TXA_2$ production itself. In addition, $TXA_2$ antagonists are not concerned in the production of prostaglandin $PGI_2$ which has anti-thrombotic activity.

SUMMARY OF THE INVENTION

In view of the above, it therefore becomes an object of the present invention to provide novel N-picolylsulfonamide derivatives for the purpose of obtaining an effective anti-thrombus agent.

The inventors of the present invention have conducted intensive studies on the synthesis of various novel N-(3-pyridylalkyl)sulfonamide derivatives and on their pharmacological activities, and have found that a specific type of the derivatives is possessed of both functions as a $TXA_2$ synthesis inhibitor and a $TXA_2$ antagonist and that the aforementioned problems involved in the prior art inhibitors and antagonists can be solved by the use of this compound. That is, since this compound has a thromboxane synthesis inhibition activity, it inhibits production of $TXA_2$ but also increases production of $PGH_2$ as described in the foregoing. However, since the compound also has a $TXA_2$ antagonism, it inhibits the $PGH_2$ activity, as well as the $TXA_2$ activity, at the receptor region. In addition, this compound can be applied to highly efficient preventive and therapeutic drugs, because it is known that $PGH_2$ accumulated in platelets and the like are converted into $PGI_2$ on the blood vessel wall and the thus converted $PGI_2$ inhibits formation of thrombi.

Particularly, in accordance with the present invention, there is provided an N-(3-pyridylalkyl)sulfonamide derivative represented by the following formula [I], a pharmacologically acceptable salt thereof, and/or a pharmacologically acceptable hydrate thereof:

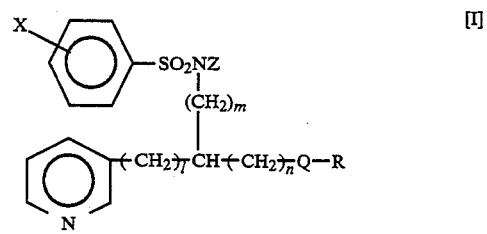

[I]

wherein X is hydrogen atom, hydroxyl group, a halogen atom, nitro group, cyano group, a lower alkyl group or a lower alkyloxyl group; R is at least one group selected from the class consisting of $-OR^1$, $-O(CH_2)_aCOOR^2$, $-OCOOR^3$, $-CR^4=CR^5-COOR^6$ and $-(CH_2)_b-COOR^7$, where each of $R^1$ to $R^7$ is independently hydrogen atom or a lower alkyl group and each of a and b is independently an integer of 0 to 4; Q is

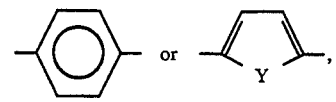

where Y is at least one group selected from the class consisting of $-S-$, $-O-$, $-NH-$, $-NR^8-$ ($R^8$ is a lower alkyl group), $-CH=CH-$, $-CH=N-$ and $-N=CH-$; Z is at least one group selected from the class consisting of hydrogen atom, a lower alkyl group, a lower alkyloxycarbonyl group, a benzyloxycarbonyl group and a formyl group; and each of l, m and n is independently an integer of 0 to 4.

In addition, according to the present invention, there are provided a thromboxane $A_2$ production inhibitor, a thromboxane $A_2$ antagonist, a prostaglandin $H_2$ antagonist, an anti-thrombus agent, a thrombus-preventing agent and an anti-allergy agent, each of which containing the just described N-(3-pyridylalkyl)sulfonamide derivative, a pharmacologically acceptable salt thereof, and/or a pharmacologically acceptable hydrate thereof.

Other objects and advantages will be made apparent as the description progresses.

DETAILED DESCRIPTION OF THE INVENTION

The gist of the present invention resides in an N-(3-pyridylalkyl)sulfonamide derivative represented by the following formula [I], a pharmacologically acceptable salt thereof, and/or a pharmacologically acceptable hydrate thereof:

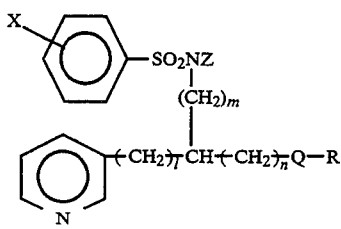

wherein X is hydrogen atom, hydroxyl group, a halogen atom, nitro group, cyano group, a lower alkyl group or a lower alkyloxyl group; R is at least one group selected from the class consisting of —OR$^1$, —O(CH$_2$)$_a$COOR$^2$, —OCOOR$^3$, —CR$^4$=C-R$^5$—COOR$^6$ and —(CH$_2$)$_b$—COOR$^7$, where each of R$^1$ to R$^7$ is independently hydrogen atom or a lower alkyl group and each of a and b is independently an integer of 0 to 4; Q is

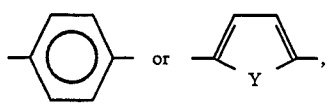

where Y is at least one group selected from the class consisting of —S—, —O—, —NH—, —NR$^8$—(R$^8$ is a lower alkyl group), —CH=CH—, —CH=N— and —N=CH—; Z is at least one group selected from the class consisting of hydrogen atom, a lower alkyl group, a lower alkyloxycarbonyl group, a benzyloxycarbonyl group and a formyl group; and each of 1, m and n is independently an integer of 0 to 4.

Regarding the definition of X in the above formula, preferred examples of the halogen atom include fluorine, chlorine and bromine and preferred examples of the alkyl moiety of the lower alkyl, lower alkyloxyl and lower alkyloxycarbonyl groups include straight chain or branched-chain alkyl groups such as methyl, ethyl, n-propyl, iso-propyl, butyl, iso-butyl, tert-butyl and the like groups.

Examples of the pharmacologically acceptable salts of the sulfonamide derivative and hydrates of the derivative represented by the formula [I] include alkali metal salts such as of sodium, potassium and the like, as well as hydrochloride and hydrates thereof.

Illustrative examples of the N-(3-pyridylalkyl)sulfonamide derivative represented by the formula [I] include compounds represented by the following formulae [II] and [III]:

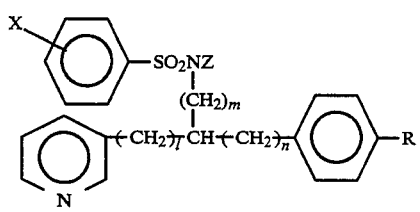

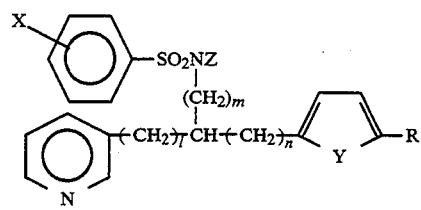

wherein X, Y, Z and R and l, m and n are the same as those in the formula [I].

Preferably, X is chlorine or methyl group, Z is hydrogen or COOCH$_2$CH$_3$ group, R is —OCH$_2$COOC$_2$H$_5$, —OCH$_2$COOH, —CH=CH—COOC$_2$H$_5$, —CH=CH—COOH, —CH$_2$CH$_2$COOC$_2$H$_5$, —CH=C(CH$_3$)—COOC$_2$H$_5$ or —CH=C(CH$_3$)COOH.

Preferably, m is 0, 1 or 2, 1 is 0 or 1, n is 0, 1 or 2, Y is —N(CH$_3$)—.

The N-(3-pyridylalkyl)sulfonamide derivative represented by the formula [I] may be obtained by allowing an amine derivative represented by the following formula [IV] to react with a benzenesulfonyl chloride derivative represented by the following formula [V] in the presence of an appropriate base (triethylamine, potassium carbonate or piridine for example) and, if necessary, further hydrolyzing the thus formed product.

The above reaction may be effected in an appropriate organic solvent such as acetone, methylene chloride, N,N-dimethyl formamide, chloroform or the like at a temperature of from 20 to 50° C. with agitation for a period of from 0.5 to 4 hours.

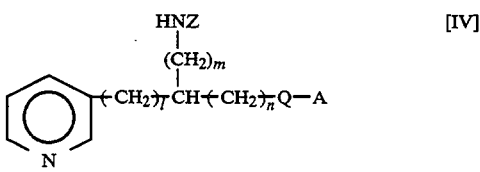

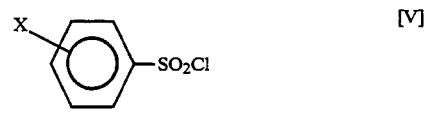

In the above formulae [IV] and [V], A is hydrogen, R, a protected hydroxyl group or a protected aldehyde group, and X, Q, z and R and l, m and n are the same as those in the formula [I].

The term "protected hydroxyl group" as used herein includes methoxymethyloxyl group, methoxyethoxymethyloxyl group and the like. The term "protected aldehyde group" as used herein includes dimethyl acetal, 1,3-dioxolane and the like.

When A is hydrogen, it may be converted into R after formylation reaction. When A is a protected aldehyde or hydroxyl group, it may be converted into R after deprotection reaction, followed by hydrolysis of the formed product if necessary.

The N-(3-pyridylalkyl) amine derivative represented by the general formula [IV] may be obtained by catalytic reduction of a nitrile derivative represented by the following formula [VI]. If necessary, it may be converted into the derivative [IV] after protecting an amino group.

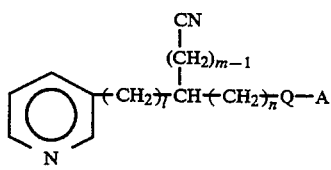
[VI]

In the above formula [VI], Q and A are the same as those described in the formulae [IV] and [I].

The N-(3-pyridylalkyl)amine derivative represented by the formula [IV] may also be obtained by reductive amination (Leuckart reaction) of a ketone derivative represented by the following formula [VII] using ammonium formate and, if necessary, hydrolyzing the thus formed formamide.

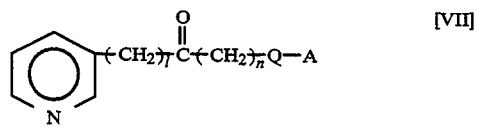
[VII]

In the above formula [VII], Q and A are the same as those described in the formula [VI].

Also, The N-(3-pyridylalkyl)amine derivative represented by the formula [IV] may be obtained by firstly subjecting a carboxylic acid derivative represented by the following formula [VIII] to Curtius rearrangement using diphenylphosphoryl azide and then by allowing the resulting product to react with an alcohol (preferably benzyl alcohol or t-butanol), followed by hydrolysis if necessary.

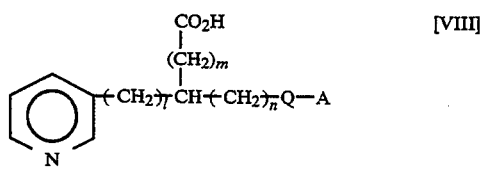
[VIII]

In the above formula [VIII], Q and A are the same as those described in the general formula [VII].

The N-(3-pyridylalkyl)sulfonamide derivative of the present invention can be applied to a thromboxane $A_2$ antagonist, a prostaglandin $H_2$ antagonist, a thromboxane $A_2$ synthesis inhibitor and effective agents for the prevention of thromboxane $A_2$-related diseases, such as a thrombus-preventing agent and an allergy-preventing agent, as well as an anti-thrombus agent and an anti-allergy agent. Though variable according to symptoms, each of these pharmaceutical preparations may be administered in a dose of generally from 10 to 600 mg, preferably from 20 to 200 mg, per day per adult, if necessary by dividing the required daily dose into 1 to 3 times depending on the condition of illness. Dosage may be effected by any optional route of administration, but most preferably by oral administration though intravenous injection is also effective.

The compound of the present invention may be made into various dosage forms, such as tablets, sugar coated tablets, powders, capsules, granules, suspensions, emulsions, parenteral solutions and the like, by using the compound as a single active ingredient or together with other active ingredients and, if necessary, by mixing it with carriers or fillers. Examples of carriers and fillers include calcium carbonate, calcium phosphate, starch, glucose, lactose, dextrin, alginic acid, mannitol, talc, magnesium stearate and the like.

EXAMPLES

The following inventive and test examples are provided to further illustrate the present invention. It is to be understood, however, that the examples are for purpose of illustration only and are not intended as a definition of the limits of the invention.

EXAMPLE 1

(1) In an atmosphere of nitrogen, 2.03 g of magnesium was suspended in 5 ml of dry tetrahydrofuran, and 16.45 g of bromo-4-methoxymethyloxybenzene which has been dissolved in dry tetrahydrofuran was added dropwise to the thus prepared suspension to form Grignard reagent. The resulting reaction mixture was diluted with 150 ml of dry tetrahydrofuran and cooled down to 0° C. To this was added dropwise 7.96 g of pyridine-3-aldehyde which has been dissolved in 20 ml of dry tetrahydrofuran. After 24 hours of stirring, saturated aqueous sodium chloride solution was added to the resulting reaction mixture. Thereafter, the organic layer was separated and the water layer was extracted with ethyl acetate.

The organic phases were combined, washed with saturated sodium chloride aqueous solution and dried using anhydrous magnesium sulfate, followed by the removal of solvents by distillation under a reduced pressure. The thus prepared residue was subjected to silica gel column chromatography to obtain 14.09 g of α-(4-methoxymethyloxyphenyl)-3-pyridylmethyl alcohol from a methanol-methylene chloride (5:95 v/v) eluate fraction.

(2) A 2.06 g portion of the thus obtained α-(4-methoxymethyloxyphenyl)-3-pyridylmethyl alcohol was dissolved in 100 ml of chloroform, and 4.38 g of activated manganese dioxide was added to the solution, followed by 24 hours of stirring at room temperature. Thereafter, the resulting reaction mixture was filtered, and solvent in the filtrate was removed by distillation under a reduced pressure to obtain 2.01 g of 4-methoxymethyloxyphenyl 3-pyridyl ketone.

(3) To 2.01 g of the thus obtained 4-methoxymethyloxyphenyl 3-pyridyl ketone which has been dissolved in 35 ml of methylene chloride and cooled down to 0° C. was added dropwise 2.01 g of titanium tetrachloride dissolved in 35 ml of methylene chloride. After 2 hours of stirring at room temperature, the resulting reaction mixture was neutralized with saturated sodium hydrogencarbonate solution and mixed with 200 ml of ethyl acetate to separate the organic layer and to extract the water layer with ethyl acetate. Thereafter, the organic phases were combined, washed with saturated sodium chloride aqueous solution and dried using anhydrous magnesium sulfate, followed by the removal of solvents by distillation under a reduced pressure to obtain 1.32 g of 4-hydroxyphenyl 3-pyridyl ketone.

(4) In 200 ml of acetone were dissolved 1.32 g of the thus obtained 4-hydroxyphenyl 3-pyridyl ketone and 1.33 g of ethyl bromoacetate. The thus prepared solution was mixed with 1.10 g of potassium carbonate and then subjected to reflux for 14 hours. The resulting reaction mixture was concentrated under a reduced pressure, mixed with saturated sodium chloride aqueous solution and extracted with methylene chloride. Thereafter, the organic layer was washed with saturated sodium chloride aqueous solution and dried using anhydrous magnesium sulfate, followed by solvent removal by distillation under a reduced pressure.

The thus prepared residue was subjected to silica gel column chromatography to obtain 1.84 g of ethyl 4-nicotinoylphenyloxyacetate from a methylene chloride eluate fraction.

(5) A mixture of 0.41 g of the thus obtained ethyl 4nicotinoylphenyloxyacetate with 0.91 g of ammonium formate was stirred at 165° C. After adding water, the reaction mixture was extracted with a solvent system of methanol and methylene chloride (5:95 v/v), the resulting water layer was boiled in azeotropy with ethanol to remove water and the ethanol soluble fraction was collected by filtration.

The filtrate was mixed with 1 ml of 6N hydrochloric acid and subjected to esterification by boiling in azeotropy with ethanol. The resulting crude product was subjected to silica gel column chromatography to obtain 0.19 g of ethyl 4-[amino-(3-pyridyl)methyl]-phenyloxyacetate from a chloroform-methanol-ammonia water (100:10:1 v/v) eluate fraction.

(6) A 0.17 g portion of p-chlorobenzenesulfonyl chloride was added to 8 ml of a methylene chloride solution containing 0.19 g of the thus obtained ethyl 4-[amino-(3pyridyl)methyl]phenyloxyacetate and 0.08 g of triethylamine, and the mixture was stirred for 13 hours. After separating organic layer by adding 2N hydrochloric acid, the remaining water layer was extracted with chloroform. Thereafter, the organic layer was washed with saturated sodium chloride aqueous solution and dried using anhydrous magnesium sulfate, followed by solvent removal by distillation under a reduced pressure. The thus prepared residue was subjected to silica gel column chromatography to obtain 0.15 g of ethyl 4-[4-chlorobenzenesulfonamide-(3-pyridyl)methyl]-phenyloxyacetate from a chloroform eluate fraction.

Spectroscopic data as shown below substantiated the following chemical structure [9].

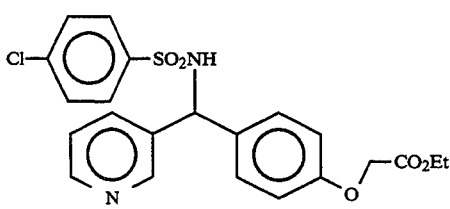

[9]

$^1$H NMR (CDCl$_3$) δ: 1.27(3H, t, J=7.0 Hz), 4.24(2H, q, J=7.0 Hz), 4.55(2H, s), 5.57(1H, br, s), 6.50–7.67(1H, m), 8.23–8.47(2H, m)

EXAMPLE 2

A 59.2 mg portion of ethyl 4-[4-chlorobenzenesulfonamide-(3-pyridyl)methyl]phenyloxyacetate obtained above was dissolved in 5 ml of ethanol and mixed with 0.13 ml of aqueous 2N sodium hydroxide solution. After 15 minutes of stirring, the resulting reaction mixture was concentrated to collect formed crystals by filtration. Thereafter, the collected crystals were recrystallized from ethanol-water solvent system and washed thoroughly with water to obtain 20.5 mg of 4-[4-chlorobenzenesulfonamide-(3-pyridyl)methyl]-phenyloxyacetic acid.

Spectroscopic data as shown below substantiated the following chemical structure [10].

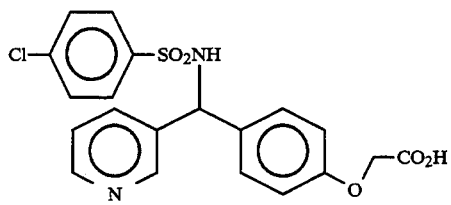

[10]

$^1$H NMR (DMSO d$_6$) δ: 4.58(2H, s), 5.59(1H, d, J=9.3 Hz), 6.77(2H, d, J=7.2 Hz), 7.00–7.70(10H, m), 8.26–8.45 (2H, m), 8.94(1H, d, J=9.3 Hz)

EXAMPLE 3

A 104 mg portion of 4-[2-(4-chlorobenzenesulfonamide-2(3-pyridyl)ethyl]phenyloxyacetic acid was mixed with 1.16 ml of aqueous 0.2N sodium hydroxide solution. The crystals were heated to melt by water bath. Thereafter, the obtained solution was cooled, as it was, to collect formed crystals by filtration. A 61 mg of sodium 4-[2-(4-chlorobenzenesulfonamide-2-(3-pyridyl)ethyl]phenyloxy acetate.

Spectroscopic data as shown below substantiated the following chemical structure [11].

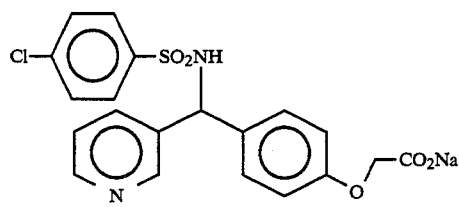

[11]

$^1$H NMR (D$_2$O:Methanol d$_4$ 1:1 v/v) δ: 2.91(2H, d, J=8 Hz), 4.39 (2H, s), 6.50–7.72(10H, m), 8.09–8.42(2H, m)

EXAMPLE 4

(1) In an atmosphere of nitrogen, 0.33 g of sodium was added to 30 ml of dry ethanol and, when sodium was dissolved, 10 ml dry ethanol solution of 2.58 g diethyl cyanomethylphosphonate was added dropwise to the sodium solution, followed by 10 minutes of stirring. To this was added dropwise 3.22 g of 4-methoxymethyloxyphenyl 3-pyridyl ketone which has been dissolved in 10 ml of dry ethanol. The resulting mixture was subjected to reflux for 72 hours, followed by solvent removal by distillation under a reduced pressure.

After adding water, the resulting mixture was extracted with ethyl acetate. Thereafter, the organic layer was washed with saturated sodium chloride aqueous solution and dried using anhydrous magnesium sulfate, followed by solvent removal by distillation under a reduced pressure. The thus prepared residue was subjected to silica gel column chromatography to obtain 3.47 g of (E+Z)-3-(4-methoxymethyloxyphenyl)-3-(3-pyridyl)acrylonitrile from a methanol-methylene chloride (5:95 v/v) eluate fraction.

(2) In 70 ml of ethanol were dissolved 3.00 g of the thus obtained (E+Z)-3-(4-methoxymethyloxyphenyl)-3-(3-pyridyl)acrylonitrile and 3.00 g of sodium borohydride. After carrying out reflux for 30 minutes, the resulting reaction mixture was concentrated under a reduced pressure, mixed with water and extracted with methylene chloride. Thereafter, the organic layer was washed with saturated sodium chloride aqueous solution and dried using anhydrous magnesium sulfate. The solvent was evaporated off under reduced pressure.

The thus prepared residue was subjected to silica gel column chromatography to obtain 2.01 g of 3-(4-methoxymethyloxyphenyl)-3-(3-pyridyl)propionitrile from a hexane-ethyl acetate (1:2 v/v) eluate fraction.

(3) In an atmosphere of nitrogen, 3.72 g of the thus obtained 3-(4-methoxymethyloxyphenyl)-3-(3-pyridyl)-propionitrile was dissolved in 150 ml of toluene and the solution was cooled down to a temperature of $-78°$ C. To this was added 30 ml toluene solution of 1.5M diisobutyl aluminium hydride, and the mixture was stirred for 2.5 hours under the same temperature condition. After adjusting to room temperature, the resulting reaction mixture was mixed with 2N sodium hydroxide aqueous solution then with Rochelle salt aqueous solution to separate organic layer.

After extracting the resulting water layer with ethyl acetate, organic layers were combined, washed with saturated sodium chloride aqueous solution and dried using anhydrous magnesium sulfate, followed by solvent removal by distillation under a reduced pressure. The thus obtained residue was subjected to silica gel column chromatography to obtain 1.93 g of 3-(4-methoxymethyloxyphenyl)-3-(3-pyridyl)propionaldehyde from a methanol-methylene chloride (3:97 v/v) eluate fraction.

(4) A 1.93 g portion of the thus obtained 3-(4-methoxymethyloxyphenyl)-3-(3-pyridyl)propionaldehyde was dissolved in 100 ml of acetone and cooled down to 0° C., followed by the addition of 3.32 ml of 2.67M Jones reagent. After stirring at 0° C. for 10 minutes, 2 ml of isopropanol was added to the resulting reaction mixture, subsequently removing the solvents by distillation under a reduced pressure. The thus treated reaction mixture was neutralized with 2N sodium hydroxide, mixed with water and then extracted with ethyl acetate.

The organic layer was washed with saturated sodium chloride aqueous solution and dried using anhydrous magnesium sulfate, followed by solvent removal by distillation under a reduced pressure. The resulting residue was subjected to recrystallization from a methylene chloride-hexane solvent system to obtain 0.94 g of 3-(4-methoxymethyloxyphenyl)-3-(3-pyridyl)propionic acid.

(5) In 30 ml of dry benzene were dissolved 933 mg of the thus obtained 3-(4-methoxymethyloxyphenyl)-3-(3-pyridyl)propionic acid, 894 mg of diphenylphosphoryl azide and 329 mg of triethylamine. After 3 hours of heating reflux, 351 mg of benzyl alcohol was added to the resulting reaction mixture, and the heating reflux was continued for additional 15 hours.

The reaction mixture was mixed with saturated sodium chloride aqueous solution and extracted with ethyl acetate. The resulting organic layer was washed with 2N hydrochloric acid, saturated sodium hydrogencarbonate aqueous solution and saturated sodium chloride aqueous solution and then dried using anhydrous magnesium sulfate, followed by solvent removal by distillation under a reduced pressure. The resulting residue was subjected to silica gel column chromatography to obtain 740 mg of N-[2-(4-methoxymethyloxyphenyl)-2-(3-pyridyl)ethyl]benzyloxycarboxyamide from a methanol-methylene chloride (3:97 v/v) eluate fraction.

(6) In an atmosphere of nitrogen, 0.74 g of the thus obtained N-[2-(4-methoxymethyloxyphenyl)-2-(3-pyridyl)ethyl]benzyloxycarboxyamide was dissolved in 30 ml of dry tetrahydrofuran. To this were added 1.34 ml hexane solution of 1.6M n-butyllithium and 0.44 g of p-chlorobenzenesulfonyl chloride, the former in dropwise manner.

After stirring for 25 minutes, the resulting reaction mixture was mixed with saturated sodium chloride aqueous solution and extracted with ethyl acetate. The resulting extract was washed with saturated sodium chloride aqueous solution and dried using anhydrous magnesium sulfate, followed by solvent removal by distillation under a reduced pressure. The resulting residue was subjected to silica gel column chromatography to obtain 0.92 g of N-(4-chlorobenzenesulfonyl)-N-[2-(4-methoxymethyloxyphenyl)-2-(3-pyridyl)ethyl]-benzyloxycarboxyamide from a methanol-methylene chloride (3:97 v/v) eluate fraction.

(7) A 0.92 g portion of the thus obtained N-(4-chlorobenzenesulfonyl)-N-[2-(4-methoxymethyloxyphenyl)-2-3-pyridyl)ethyl]benzyloxycarboxyamide was dissolved in 20 ml of methanol, and 1 ml of 6N hydrochloric acid was added to the solution. After stirring at 60° C. for 3.5 hours, the resulting reaction mixture was concentrated under a reduced pressure, mixed with ethyl acetate and water and then adjusted to alkalinity with saturated solution of sodium hydrogencarbonate.

After separating organic layer, the reaction product was extracted from the remaining water layer with ethyl acetate, washed with saturated sodium chloride aqueous solution and then dried using anhydrous magnesium sulfate. Thereafter, the solvent was removed by distillation under a reduced pressure to obtain 0.81 g of N-(4-chlorobenzenesulfonyl)-N-[2-(4-hydroxyphenyl)-2-(3-pyridyl)ethyl]benzyloxycarboxyamide.

(8) In 40 ml of acetone were suspended 0.81 g of the thus obtained N-(4-chlorobenzenesulfonyl)-N-[2-(4-hydroxyphenyl)-2-(3-pyridyl)ethyl]benzyloxycarboxyamide, 0.23 g of potassium carbonate and 0.28 g of ethyl bromoacetate. The thus prepared suspension was stirred at room temperature for 10 hours and then subjected to 5 hours of heating reflux. The resulting reaction mixture was concentrated under a reduced pressure, mixed with water and then extracted with methylene chloride.

The resulting organic layer was washed with saturated sodium chloride aqueous solution and dried using anhydrous magnesium sulfate, followed by solvent removal by distillation under a reduced pressure. The resulting residue was subjected to silica gel column chromatography to obtain 0.23 g of ethyl 4-{2-[N-benzyloxycarbonyl-N-(4-chlorobenzenesulfonyl)amino]-1-(3-pyridyl)ethyl}phenyloxyacetate from a methanol-methylene chloride (3:97 v/v) eluate fraction.

(9) In 10 ml of ethanol were suspended 0.23 g of the thus obtained ethyl 4-{2-[N-benzyloxycarbonyl-N-(4-chlorobenzenesulfonyl)amino]-1-(3pyridyl)ethyl} phenyloxyacetate and 0.14 g of 10% palladium-carbon. The thus prepared suspension was subjected to 14 hours of catalytic reduction reaction at ambient temperature and pressure. The resulting reaction mixture was filtered to collect filtrate, and the solvent in the filtrate was removed by distillation under a reduced pressure. Thereafter, the resulting residue was applied to silica gel preparative TLC and developed twice with methanol-methylene chloride (5:95 v/v) to obtain 0.12 g of ethyl 4-[2-(4-chlorobenzenesulfonamido)-1-(3-pyridyl- )ethyl]phenyloxyacetate from the band at an Rf value of from 0.65 to 0.43.

Spectroscopic data as shown below substantiated the following chemical structure [12].

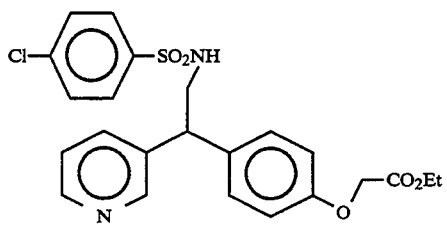

[12]

$^1$H NMR (CDCl$_3$) δ: 1.26(3H, t, J=7.0 Hz), 3.51(2H, dd, J=6.5, 6.5 Hz), 4.04(1H, t, J=6.5 Hz), 4.22(2H, q, J=7.0 Hz), 4.54(2H, s), 5.51(1H, t, J=6.5 Hz), 6.63–7.91 (10H, m), 8.18–8.48(2H, m)

EXAMPLE 5

A 81 mg portion of ethyl 4-[2-(4-chlorobenzenesulfonamido)-1-(3-pyridyl)ethyl]phenyloxyacetate obtained above was dissolved in 5 ml of ethanol, 1.0 ml of 2 N sodium hydroxide was added to the solution and the mixture was stirred for 1 hour. The resulting reaction mixture was concentrated under a reduced pressure, neutralized with 2N hydrochloric acid, mixed with water and then extracted with ethanol-methylene chloride (5:95 v/v). The extract was washed with saturated aqueous sodium chloride solution and then dried using anhydrous magnesium sulfate. Thereafter, the solvents were removed by distillation under a reduced pressure to obtain 56 mg of 4-[2-(4-chlorobenzenesulfonamido)-1-(3-pyridyl)ethyl]phenyloxyacetic acid.

Spectroscopic data as shown below substantiated the following chemical structure [13].

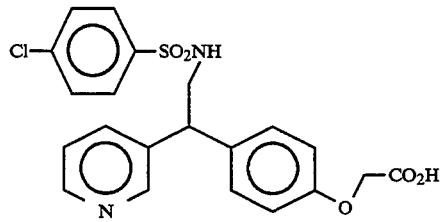

[13]

$^1$H NMR (CDCl$_3$-Methanol d$_4$ 9:1 v/v) δ: 3.40(2H, d, J=8.0 Hz), 4.14(1H, t, J=8.0 Hz), 4.55(2H, m), 6.78(2H, d, J=9.0 Hz), 7.03(2H, d, J=9.0 Hz), 7.17–8.80(8H, m)

EXAMPLE 6

(1) An appropriate amount of Raney nickel was suspended in 15 ml of saturated ammonical methanol solution, 0.54 g of 3-(4-methoxymethyloxyphenyl)-3-(3-pyridyl)propionitrile was added to the suspension and the mixture was stirred for 18 hours under 15 atmospheric pressure in an atmosphere of hydrogen. The resulting reaction mixture was filtered and the filtrate was concentrated under a reduced pressure. The thus prepared residue was subjected to silica gel column chromatography to obtain 0.49 g of 3-(4-methoxymethyloxyphenyl)-3-(3-pyridyl)propylamine from ammonia water-methanol-chloroform (1:10:100 v/v) eluate fraction.

(2) A 0.49 g portion of the thus obtained 3-(4-methoxymethyloxyphenyl)-3-(3-pyridyl)propylamine and 0.20 g of triethylamine were dissolved in 15 ml of methylene chloride, and 0.42 g of chlorobenzenesulfonyl chloride was added to the thus prepared solution at 0° C. After 48 hours of stirring at room temperature, the resulting reaction mixture was poured in water to separate organic layer, and the remaining water layer was extracted with methylene chloride. Thereafter, the organic phases were combined, washed with saturated aqueous sodium chloride solution and dried using anhydrous magnesium sulfate, followed by solvent removal by distillation under a reduced pressure.

The resulting residue was subjected to silica gel column chromatography to obtain 0.48 g of N-[3-(4-methoxymethyloxyphenyl)-3-(3-pyridyl)propyl]-4-chlorobenzene sulfonamide from a methanol-methylene chloride (3:97 v/v) eluate fraction.

(3) In an atmosphere of nitrogen, 1.22 g of the thus obtained N-[3-(4-methoxymethyloxyphenyl)-3-(3-pyridyl)propyl]-4-chlorobenzenesulfonamide was dissolved in 30 ml of dry tetrahydrofuran, and the solution was cooled down to a temperature of −15° C. To this was added in dropwise manner 1.6M n-butyllithium which has been dissolved in hexane. After 30 minutes of stirring, 0.54 g of ethyl chlorocarbonate dissolved in 10 ml of dry tetrahydrofuran was further added in dropwise manner, and the stirring was continued for additional 24 hours.

The resulting reaction mixture was mixed with water and extracted with ethyl acetate. Thereafter, the extract was washed with saturated aqueous sodium chloride solution and dried using anhydrous magnesium sulfate, followed by solvent removal by distillation under a reduced pressure. The resulting residue was subjected to silica gel column chromatography to obtain 1.03 g of N-ethoxycarbonyl-N-[3-(4-methoxymethyloxyphenyl)-3-(3-pyridyl)propyl]-4-chlorobenzene sulfonamide from a methanol-methylene chloride (2:98 v/v) eluate fraction.

(4) A 1.03 g portion of the thus obtained N-ethoxycarbonyl-N-[3-(4 -methoxymethyloxyphenyl)-3-(3-pyridyl)propyl]-4-chlorobenzenesulfonamide was dissolved in 25 ml of ethanol. After adding 1 ml of 6N hydrochloric acid, the solution was stirred at 60° C. for 1.5 hours. The resulting reaction mixture was concentrated under a reduced pressure, mixed with methylene chloride and then adjusted to alkalinity with saturated sodium hydrogencarbonate aqueous solution to separate organic layer. After extraction with chloroform, the extract was washed with saturated sodium chloride aqueous solution and dried using anhydrous magnesium sulfate. Thereafter, the solvent was removed by distillation under a reduced pressure to obtain 0.80 g of N-ethoxycarbonyl-N-[3-(4-hydroxyphenyl)-3-(3-pyridyl)propyl]-4-chlorobenzene sulfonamide.

(5) In an atmosphere of nitrogen, 0.30 g of the thus obtained N-ethoxycarbonyl-N-[3-(4-hydroxyphenyl)-3-(3-pyridyl)propyl]-4-chlorobenzenesulfonamide was dissolved in dry tetrahydrofuran. At −10° C., 1.6M n-butyllithium which has been dissolved in hexane was added in dropwise manner. After 30 minutes of stirring, 0.14 g of ethyl bromoacetate dissolved in 10 ml of dry tetrahydrofuran was added to the mixture in dropwise manner. After further adding 2 ml of dry dimethyl sulfoxide, the mixture was stirred for 24 hours.

The resulting reaction mixture was mixed with saturated aqueous sodium chloride solution and extracted with ethyl acetate. The extract was washed with saturated sodium chloride aqueous solution and dried using anhydrous magnesium sulfate, followed by solvent removal by distillation under a reduced pressure. Thereafter, the resulting residue was applied to silica gel preparative TLC and developed with methanol-methylene chloride (4:96 v/v) to obtain 0.10 g of ethyl 4-{3-[N-(4-chlorobenzenesulfonyl)-N-ethoxycarbonylamino)]-1-(3-pyridyl)propyl}phenyloxyacetate from the band at an Rf value of from 0.65 to 0.45.

Spectroscopic data as shown below substantiated the following chemical structure [14].

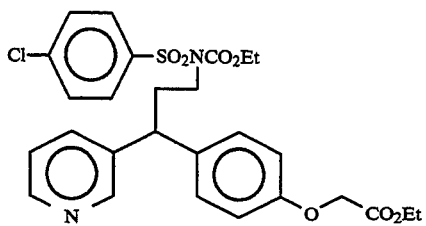

[14]

¹H NMR (CDCl₃) δ: 1.15(3H, t, J=7.0 Hz), 1.28(3H, t, J=7.0 Hz), 2.47(2H, q, J=7.5 Hz), 3.75–4.45(7H, m), 4.55(2H, s), 6.67–8.00(10H, m), 8.25–8.57(2H, m)

EXAMPLE 7

A 0.10 g portion of ethyl 4-{3-[N-(4-chlorobenzenesulfonyl)-N-ethoxycarbonylamino)]-1-(3-pyridyl)propyl}phenyloxyacetate obtained above was dissolved in 4 ml of ethanol, and the solution was mixed with 7.1 ml of 0.1N sodium hydroxide. After 1.5 hours of stirring, the resulting reaction mixture was concentrated under a reduced pressure, neutralized with 2N hydrochloric acid and the precipitated crystals were collected by filtration to obtain 58 mg of 4-[3-(4-chlorobenzenesulfonamido)-1-(3-pyridyl)propyl]phenyloxyacetic acid.

Spectroscopic data as shown below substantiated the following chemical structure [15].

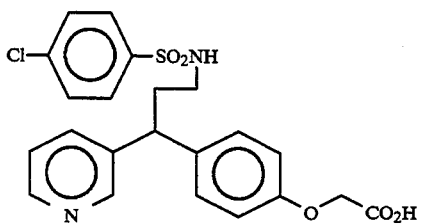

[15]

¹H NMR (DMSO d₆) δ: 4.60(2H, s), 6.68–7.95(10H, m), 8.25–8.55(2H, m)

EXAMPLE 8

(1) In an atmosphere of nitrogen, 2.34 g of diisopropylamine was dissolved in 30 ml of dry tetrahydrofuran, and the solution was cooled down to a temperature of −10° C. To this was added 1.6M n-butyllithium which has been dissolved in 14.9 ml of hexane. After 20 minutes of stirring, 4.14 g of hexamethylphosphoric triamide which has been dissolved in 10 ml of dry tetrahydrofuran was added to the mixture, and the stirring was continued for another 5 minutes. To this was added in dropwise manner 2.15 g of 3-methylpyridine dissolved in 15 ml of dry tetrahydrofuran. After 10 minutes of stirring, 2.15 g of methyl 4-methoxymethyloxybenzoate which has been dissolved in 15 ml of tetrahydrofuran was further added in dropwise manner, and the stirring was continued for 15 hours.

The resulting reaction mixture was mixed with saturated sodium chloride aqueous solution to separate organic layer, and the remaining water layer was extracted with ethyl acetate. Thereafter, the organic layers were combined, washed with saturated sodium chloride aqueous solution and dried using anhydrous magnesium sulfate, followed by solvent removal by distillation under a reduced pressure. The resulting residue was subjected to column chromatography to obtain 1.24 g of 1-(4-methoxymethyloxyphenyl)-2-(3-pyridyl)ethanone from a n-hexane-ethyl acetate eluate fraction.

(2) From the thus obtained 1-(4-methoxymethyloxyphenyl)-2-(3-pyridyl)ethanone, 4-[1-(4-chlorobenzenesulfonamido)-4-(3-pyridyl)-3-butyl]phenyloxyacetic acid was obtained in the same manner as in Example 6.

Spectroscopic data as shown below substantiated the following chemical structure [16].

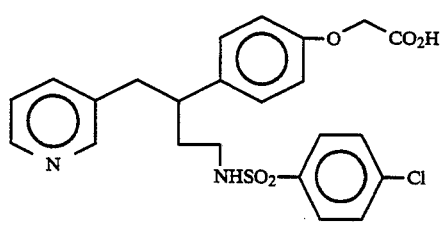

[16]

¹H NMR (DMSO d₆) δ: 1.45–2.00(3H, m), 2.60–3.00(5H, m), 4.58(2H, s), 6.62–7.82(11H, m), 8.09–8.38(2H, m)

EXAMPLE 9

A 0.40 g portion of ethyl 4-{1-[N-(4-chlorobenzenesulfonyl)-N-ethoxycarbonylamino]-4-(3-pyridyl)-3-butyl}phenyloxyacetate was dissolved in 10 ml of ethanol. To this was added aqueous 2N sodium hydroxide solution, followed by 4 hours of stirring at room temperature. After adjusting to acidity with 2N hydrochloric acid, the solution was subjected to esterification by boiling in azeotropy with ethanol. After adding water, the resulting reaction mixture was extracted with methylene chloride, and the organic layer was washed with saturated sodium chloride aqueous solution and dried using anhydrous magnesium sulfate, followed by solvent removal by distillation under a reduced pressure.

Thereafter, the resulting residue was applied to silica gel preparative TLC and developed with methanol-methylene chloride (5:95 v/v) to obtain 0.17 g of ethyl 4-[1-(4-chlorobenzenesulfonyl)-4-(3-pyridyl)-3-butyl]phenyloxyacetate from a band on the TLC having an Rf range of from 0.37 to 0.50.

Spectroscopic data as shown below substantiated the following chemical structure [17].

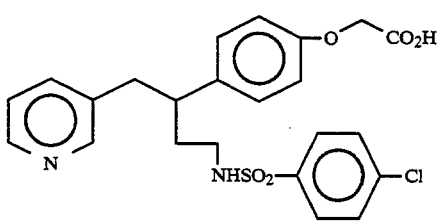

[17]

¹H NMR (CDCl₃) δ: 1.26(3H, t, J=7.5 Hz), 1.57–2.16(2H, m), 2.44–3.17(5H, m), 4.23(2H, q, J=7.5 Hz), 4.54(2H, s), 5.70(1H, t, J=6.0 Hz), 6.57–7.83(10H, m), 8.02–8.44(2H, m)

EXAMPLE 10

1) In 70 ml of acetone were suspended 5.00 g of p-cresol, 7.72 g of ethyl bromoacetate and 6.39 g of potassium carbonate, and the resulting mixture was refluxed for 12 hours. After the solvent was distilled off under reduced pressure, water was added to the mixture, followed by extraction with methylene chloride. The organic phase was washed with in aqueous 2N sodium hydroxide solution and then with saturated sodium chloride solution, which was then dried over magnesium sulfate. On evaporation of the solvent under reduced pressure, 8.67 g of ethyl 4-methylphenoxyacetate was produced.

2) In 30 ml of carbon tetrachloride were dissolved 1.00 g of the ester obtained, 1.01 g of n-bromosuccinimide and 0.01 g of benzoyl peroxide, and the resulting mixture was refluxed for 3 hours. After completion of the reaction, the crystalline deposited was filtered off. The filtrate was concentrated under reduced pressure, to obtain quantitatively ethyl 4-(bromomethyl)phenoxyacetate. The bromo compound was subjected to the following reaction, without further purification.

3) In argon atmosphere, 7.60 g of diisopropylamine was dissolved in 100 ml of dry tetrahydrofuran, followed by dropwise addition of 1.55M n-butyl lithium in 48.4 ml of hexane in solution at −20° C., which was then agitated at the same temperature for 15 minutes, subsequently followed by cooling to −78° C. and by subsequent dropwise addition of 15.48 g of 2-(3-pyridyl)-2-(trimethylsiloxy)acetonitrile dissolved in 150 ml of dry tetrahydrofuran over 10 minutes. After agitation at the same temperature for 30 minutes, the addition of 20.50 g of ethyl 4-(bromomethyl)phenoxyacetate dissolved in 30 ml of tetrahydrofuran over 10 minutes, the temperature was gradually raised from −78° C. to room temperature, followed by stirring overnight. Then, 1.0M tetra-n-butylammonium fluoride in 75.1 ml of tetrahydrofuran in solution was added, followed by agitation for five hours. To the resulting reaction mixture was added aqueous saturated solution of sodium chloride, followed by separation of the organic phase, which was then extracted with ethyl acetate from aqueous phase. The organic phases were combined, then washed in aqueous saturated solution of sodium chloride and dried over magnesium sulfate. The solvent was distilled off under reduced pressure. The residue obtained was subjected to chromatography on a silica gel column, to yield 13.20 g of ethyl 4-[2-oxo-2-(3-pyridyl)ethyl]phenoxyacetate from a fraction eluted with methanol-chloroform (2:98 v/v).

4) At 140° C., 4.60 g of ethyl 4-[2-oxo-2-(3-pyridyl)ethyl]phenoxyacetate was heated and agitated together with 9.69 g of ammonium formate for 1.5 hours. To the resulting reaction mixture was added water, followed by extraction with methylene chloride. The organic phase was then washed in aqueous saturated solution of sodium chloride, and dried over magnesium sulfate. The solvent was evaporated off under reduced pressure. The residue obtained was subjected to chromatography on a silica gel column, to yield 1.39 g of ethyl 4-[2-(formamide)-2-(3-pyridyl)ethyl]phenoxyacetate from a fraction eluted with methanol-methylene (2:98 v/v).

5) To 1.39 g of ethyl 4-[2-formamido-2-(3-pyridyl)ethyl]phenoxyacetate in 40 ml of ethanol in solution was added 4.30 ml of 2N aqueous sodium hydroxide solution, followed by agitation at room temperature for one hour. After completion of the reaction, the reaction mixture was boiled with ethanol. Then, the mixture was dried under reduced pressure with a vacuum pump. The sodium salt obtained was dissolved in a mixed solvent of 10 ml of water and 10 ml of dioxane, followed by addition of 10 ml of 6N hydrogenchloride. The resulting mixture was heated to 90° C., and stirred for 12 hours. Azeotropic process of the reaction mixture of such amino acid was repeated with ethanol, which again realized ethylesterification. After completion of the reaction, an aqueous solution of sodium hydrogencarbonate was added, followed by extraction with ethyl acetate and by subsequent washing of the organic phase with saturated solution of sodium chloride, drying over magnesium sulfate and evaporation of the solvent under reduced pressure, to produce 0.91 g of ethyl 4-[2-amino-2-(3pyridylethyl]phenoxyacetate.

6) In 15 m of methylene chloride were dissolved 0.19 g of ethyl 4-[2-amino-2-(3-pyridyl)ethyl]phenoxyacetate and 0.09 g of triethylamine, followed by addition of 0.17 g of p-toluene sulfonylchloride, and stirred at room temperature for 15 hours. To the reaction mixture was added water, and the organic phase was then separated, which was extracted from aqueous phase with methanol-methylene chloride (5:95 v/v). The organic phases were combined and washed with 2N hydrogen chloride, followed by washing in aqueous saturated sodium chloride solution and drying over magnesium sulfate. Then, the solvent was evaporated off under reduced pressure. The residue obtained was subjected to preparative TLC on silica gel which was developed with methanol-methylene chloride (5:95 v/v). From the band at an Rf value of 0.35 to 0.45, 0.13 g of ethyl 4-[2-(4-toluene sulfonamido)-2-(3-pyridyl)ethyl]phenoxyacetate was obtained, which spectrometric data supports the structure of [18] as follows.

Chemical Formula 18

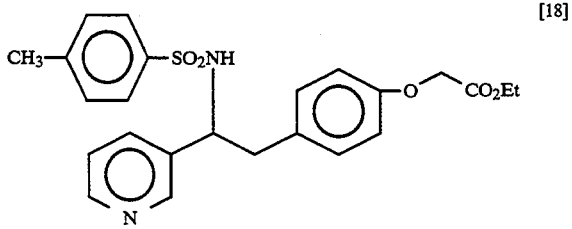

¹H NMR (CDCl₃) δ: 1.26(3H, t, J=7.5 Hz), 2.33(3H, s), 2.89(2H, d, J=7.5 Hz), 4.22(2H, q, J=7.5 Hz), 4.45(1H, dt, J=7.5 Hz, 7.5 Hz), 4.50(2H, s), 6.19(1H, d, J=7.5 Hz), 6.45–7.56(10H, m), 8.09–8.42(2H, m)

EXAMPLE 11

Ethyl 4-[2-(4-toluene sulfonamido)-2-(3-pyridyl)ethyl]phenoxyacetate (90 mg) was dissolved in 2 ml of ethanol and 2 ml of tetrahydrofuran, followed by addition of 0.30 ml of aqueous 2N sodium hydroxide solution, and stirred at room temperature for one hour. The solvent was concentrated under reduced pressure, and neutralized with 2N hydrogen chloride. Then, the crystalline deposited was taken out by filtration, to yield 80 mg of ethyl 4-[2-(4-toluene sulfonamido)-2-(3-pyridyl)-ethyl]phenoxyacetic acid.

The spectrometric data thereof supports the structure of [19] as follows.

Chemical Formula 19

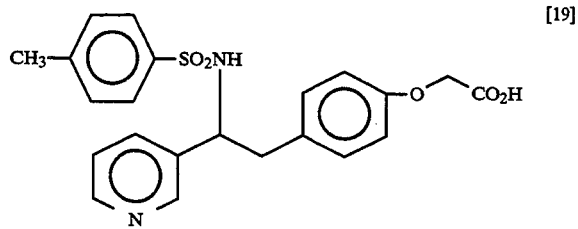

$^1$H NMR(DMSO-d$_6$) δ: 2.29(3H, s), 2.80(2H, d, J=7.0 Hz), 4.42(1H, dt, J=7.0, 7.0 Hz), 4.59(2H, s), 6.54–7.66(11H, m), 8.18–8.42(2H, m)

EXAMPLE 12

In 15 ml of methylene chloride were dissolved 0.19 g of the ethyl 4-[2-amino-2-(3-pyridyl)ethyl]phenoxyacetate synthesized as in Example 10 5) and 0.09 g of triethylamine, followed by addition of 0.16 g of benzenesulfonyl chloride, and stirred at room temperature for 15 hours. To the reaction mixture was added water, and the organic phase was separated, which was then extracted with methanol-methylene chloride (5:95 v/v) from aqueous phase. The organic phases were combined and washed with 2N hydrogen chloride, followed by washing in aqueous saturated sodium chloride solution and drying over magnesium sulfate. Then, the solvent was evaporated off under reduced pressure. The residue obtained was subjected to preparative TLC on silica gel which was developed with methanol-methylene chloride (5:95 v/v). From the band at an Rf value of 0.25 to 0.38, 0.11 g of ethyl 4-[2-benzenesulfonamido)-2-(3-pyridyl)ethyl]phenoxyacetate was obtained, which spectrometric data supports the structure of [20] as follows.

Chemical Formula 20

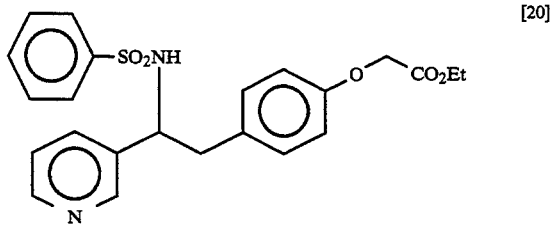

$^1$H NMR (CDCl$_3$) δ: 1.26(3H, t, J=7.5 Hz), 2.91(2H, d, J=7.5 Hz), 4.23(2H, q, J=7.5 Hz), 4.48(1H, dt, J=7.5, 7.5 Hz), 4.52(2H, s), 6.20(1H, d, J=7.5 Hz), 6.44–7.73(11H, m), 8.16–8.45(2H, m)

EXAMPLE 13

Ethyl 4-[2-benzenesulfonamido-2-(3-pyridyl)ethyl]-phenoxyacetate (70 mg) was dissolved in 2 ml of ethanol and 2 ml of tetrahydrofuran, followed by addition of 0.30 ml of aqueous 2N sodium hydroxide solution, and stirred at room temperature for one hour. The solvent was concentrated under reduced pressure, and neutralized with 2N hydrogen chloride. Then, the crystalline deposited was taken out by filtration and recrystallized in aqueous ethanol, to yield 15 mg of ethyl 4-[2-benzenesulfonamido-2-(3-pyridyl)ethyl]phenoxyacetic acid. The spectrometric data thereof supports the structure of [21] as follows.

Chemical Formula 21

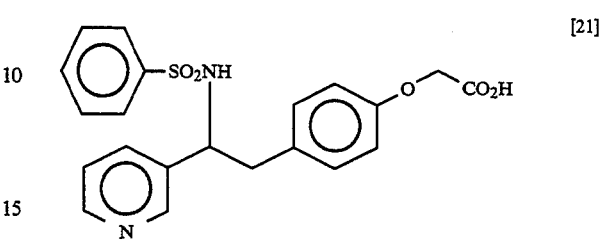

$^1$H NMR (DMSO-d$_6$) δ: 2.83(2H, d, J=7.5 Hz), 4.33–4.80(1H, m), 4.60(2H, s), 6.61–7.76(12H, m), 8.21–8.57(2H, m)

EXAMPLE 14

1) In 200 ml of carbon tetrachloride were dissolved 9.18 g of ethyl 4-methylcinnamate, 9.45 g of N-bromosuccinimide and 0.12 g of benzoyl peroxide, and refluxed for 14 hours. After completion of the reaction, the crystalline deposited was filtered off, and the filtrate was then concentrated under reduced pressure to quantitatively produce ethyl 4-bromomethylcinnamate. The bromo compound was used in the following reaction without further purification.

2) In argon atmosphere, 4.88 g of diisopropylamine was dissolved in 100 ml of dry tetrahydrofuran, followed by dropwise addition of 1.55M n-butyl lithium in 31.1 ml of hexane in solution at −20° C. After stirring at the same temperature for 10 minutes and then cooling down to -78° C., 9.96 g of 2-(3-pyridyl)-2-(trimethylsiloxy)acetonitrile dissolved in 100 ml of dry tetrahydrofuran was added dropwise. After stirring at the same temperature for one hour, 12.99 g of ethyl 4-bromomethylcinnamate dissolved in 100 ml of dry tetrahydrofuran was added, followed by gradual temperature rise from -78° C. to room temperature and stirring overnight. 1.0M Tetra-n-butylammonium fluoride in 48.3 ml of tetrahydrofuran in solution was added and stirred for 3.5 hours. To the reaction mixture was added saturated aqueous sodium chloride solution, and the organic phase was separated, which was then extracted with ethyl acetate from aqueous phase. The organic phases were combined and washed with saturated aqueous sodium chloride solution, followed by drying over magnesium sulfate. Then, the solvent was distilled off under reduced pressure. The residue obtained was subjected to chromatography on a silica gel column, and 6.21 g of ethyl 4-[2-oxo-2-(3-pyridyl)ethyl]cinnamate was obtained from a fraction eluted with methanol-methylene chloride (2:98 v/v).

3) Ethyl 4-[2-oxo-2-(3-pyridyl)ethyl]cinnamate (1.0 g) and ammonium formate (4.28 g) were stirred at 140° C. for four hours. To the reaction mixture was added water, followed by extraction with methylene chloride and washing of the organic phase in saturated aqueous sodium chloride solution, and dried over magnesium sulfate. Then, the solvent was evaporated off under reduced pressure. The residue obtained was subjected to chromatography on a silica gel column, to yield 0.72 g of ethyl 4-[2-formamido-2-(3-pyridyl)ethyl]cinnamate from a fraction eluted with methanol:methylene chloride (4:96 v/v).

4) Ethyl 4-[2-formamido-2-(3-pyridyl)ethyl]cinnamate (0.40 g) was dissolved in a mixed solvent of 10 ml of ethanol, 10 ml of tetrahydrofuran and 8 ml of water, followed by addition of 0.40 ml of concentrated sulfuric acid and heating to 65° C., and stirred for 17 hours. After completion of the reaction, the solvent was evaporated under reduced pressure, followed by addition of $CH_2Cl_2$ and water and subsequent gradual addition of saturated aqueous solution of sodium hydrogencarbonate to adjust the mixture to weak alkalinity. The organic phase was separated and extracted from aqueous phase with methanol-methylene chloride (5:95 v/v), followed by washing in saturated aqueous sodium chloride solution, drying over magnesium sulfate and evaporation of the solvent, to produce 0.35 g of ethyl 4-[2-amino-2-(3-pyridyl)ethyl]cinnamate.

5) A solution of ethyl 4-[2-amino-2-(3-pyridyl)ethyl]cinnamate (0.35 g) and triethylamine (0.14 g) in methylene chloride was cooled down to 0° C., followed by addition of 0.30 g of chlorobenzenesulfonyl chloride, and stirred at room temperature for 24 hours. To the reaction mixture was added water, which was then adjusted to weak acidity with 2N hydrogen chloride. Then, the organic phase was separated and extracted with methanol-methylene chloride (5:95 v/v) from aqueous phase, and the combined organic phases were washed in saturated aqueous sodium chloride solution, followed by drying over magnesium sulfate. The solvent was then evaporated under reduced pressure, to obtain 0.22 g of ethyl 4-[2-(4-chlorobenzenesulfonamido-2-(3-pyridyl)ethyl]cinnamate from a fraction eluted with methanol:methylene chloride (5:95 v/v). The spectrometric data thereof supports the structure of [22] as follows.

$^1$H NMR ($CDCl_3$-methanol $d_4$; 5:1v/v) δ: 1.34(3H, t, J=7.5 Hz), 3.00(2H, d, J=7.5 Hz), 4.27(2H, q, J=7.5 Hz), 4.50(1H, dt, J=7.5, 7.5 Hz), 6.39(1H, d, J=16 Hz), 6.85–7.61(11H, m), 7.60(1H, d, J=16 Hz), 8.25–8.48(2H, m)

Chemical Formula 22

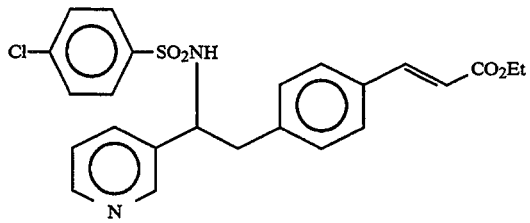

[22]

EXAMPLE 15

Ethyl 4-[2-(4-chlorobenzenesulfonamido-2-(3-pyridyl)ethyl]cinnamate (110 mg) was dissolved in a mixed solvent of 5 ml of ethanol and 15 ml of tetrahydrofuran, followed by addition of 0.24 ml of aqueous 2N sodium hydroxide solution, and stirred at room temperature for 40 hours. The reaction mixture was concentrated under reduced pressure, which was then adjusted to weak acidity with 2N hydrogen chloride. Then, the crystalline deposited was taken out by filtration, followed by washing in water and drying, to yield 70 mg of 4-[2-(4-chlorobenzenesulfonamido]-2-(3-pyridyl)ethyl]cinnamic acid. The spectrometric data thereof supports the structure of [23] as follows.

Chemical Formula 23

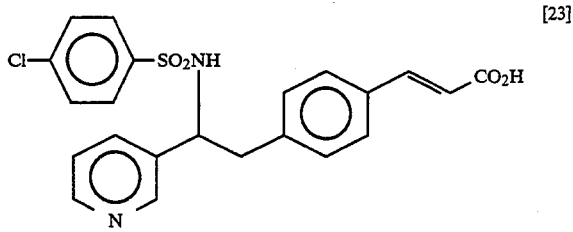

[23]

$^1$H NMR (DMSO-$d_6$) δ: 2.91(2H, d, J=7.7 Hz), 4.40–4.73(1H, m), 6.46(1H, d, J=16, 3 Hz), 7.07–7.78(11H, m), 8.25–8.74(2H, m)

EXAMPLE 16

Nickel chloride (20 mg) was suspended in 1 ml of methanol and 9 ml of methylene chloride, followed by gradual addition of 120 mg of sodium borohydride at 0° C. At the same temperature, ethyl 4-[2-(4-chlorobenzenesulfonamido)-2(3-pyridyl)ethyl]cinnamate dissolved in 0.5 ml of methanol and 4.5 ml of methylene chloride was added and stirred at room temperature for eight hours. To the reaction mixture was added dropwise 2N hydrogen chloride at 0° C., until the mixture became acidic. The organic phase was separated and extracted with methanol-methylene chloride (5:95 v/v). The organic phases were combined and washed in saturated aqueous sodium chloride solution, followed by drying over magnesium sulfate. Then, the solvent was evaporated under reduced pressure. The residue obtained was subjected to chromatography on a silica gel column which was eluted with methanol-methylene chloride (5:95 v/v) for purification, followed by recrystallization in methylene chloride-hexane, to produce 70 mg of ethyl 3-(4-[2-(4-chlorobenzenesulfonamido)-2(3-pyridyl)ethyl]phenyl}propionate. The spectrometric data thereof supports the structure of [24] as follows.

$^1$H NMR ($CDCl_3$) δ: 1.24(3H, t, J=7.0 Hz), 2.58(2H, t, J=7.0 Hz), 2.79–3.06(4H, m), 4.14(2H, q, J=7.0 Hz), 4.55(1H, dt, J=7.0 Hz), 5.03(1H, d, J=7.0 Hz), 6.73–7.60(10H, m), 8.28–8.54(2H, m)

Chemical Formula 24

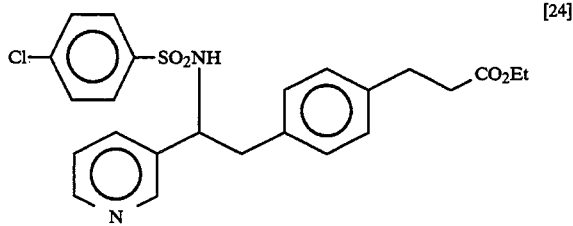

[24]

EXAMPLE 17

Ethyl 3-{4-[2-(4-Chlorobenzenesulfonamido)-2-(3-pyridyl)ethyl]phenyl}propionate (49 mg) was dissolved in a mixed solvent of 1 ml of ethanol and 1 ml of tetrahydrofuran, followed by addition of 0.30 ml of aqueous 2N sodium hydroxide solution, and stirred at 60° C. for 20 minutes. The reaction mixture was concentrated under reduced pressure, which was then adjusted to neutrality with 2N hydrogen chloride. Then, the crystalline deposited was taken out by filtration, and washed in water, followed by drying, to produce 30 mg of 3-{4-[2-(4-chlorobenzenesulfonamido)-2(3-pyridyl)ethyl]phenyl} propionic acid. The spectrometric data supports the structure of [25] as follows.

$^1$H NMR(DMSO-d$_6$) δ: 2.80(2H, t, J=7.5 Hz), 4.34–4.75(2H, m), 6.92–7.73(10H, m), 8.2–8.73(2H, m)

Chemical Formula 25

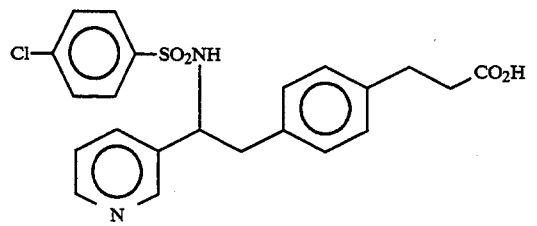

[25]

EXAMPLE 18

1) Pyridine-3-aldehyde (44.4 g), trimethylsilyl cyanide (47.5 g) and zinc iodide (0.01 g) were mixed, and stirred under heating at 90° C. for 1.5 hours. The resulting reaction mixture was fractionated (at 5 mmHg, and 122 to 132° C.), to produce 2-(3-pyridyl)-2-(trimethylsiloxy)acetonitrile (39.8 g).

2) Methyl p-toluylate (9.3 g) was dissolved in 200 ml of carbon tetrachloride, followed by addition of N-bromosuccinimide (12.2 g) and benzoyl peroxide (0.15 g), and refluxed under heating overnight. The reaction mixture obtained was cooled and filtered, to produce methyl 4-bromomethyl benzoate (13.5 g).

3) A solution of diisopropylamine (4.5 g) in dry tetrahydrofuran (60 ml) was cooled to −35 to 31 40 ° C., followed by addition of 1.5M n-butyl lithium in 30 ml of hexane in solution, and stirred for 30 minutes, to produce lithium diisopropylamide. To the solution was added a solution of 2-(3-pyridyl)-2-(trimethylsiloxy)acetonitrile in dry tetrahydrofuran at −78 ° C., and stirred at the same temperature for 30 minutes. After the addition of a solution of methyl 4-bromomethyl benzoate in dry tetrahydrofuran at − 78 ° C., stirring was effected overnight at −78 ° C. to room temperature. To the reaction mixture obtained was added 1.0 M tetra-n-butylammonium fluoride in 40 ml of dry tetrahydrofuran in solution and stirred at room temperature for 3.5 hours. The reaction solution was poured into saturated aqueous sodium chloride solution, and after separation of the organic phase, the aqueous phase was extracted with ethyl acetate. The combined organic phases were washed in saturated aqueous sodium chloride solution, followed by drying over magnesium sulfate and distillation of the solvent. The residue was subjected to chromatography on a silica gel column. A fraction eluted with chloroform-methanol (50:1 v/v) was recrystallized in n-hexane chloroform to produce 3.0 g of methyl 4-[2-oxo-2-(3-pyridyl)ethyl]benzoate.

4) To 2.00 g of methyl 4-[2-oxo-2-(3-pyridyl)-]benzoate was added 14.8 g of ammonium formate, for reaction at 150° C. for four hours, and followed by addition of water after cooling and extraction with chloroform. The organic phase was washed in saturated aqueous sodium chloride solution, dried over magnesium sulfate, followed by distillation of the solvent, to produce the residue. The residue was subjected to chromatography on a silica gel column, which was then eluted with chloroform-methanol (25:1 ) to produce 0.81 g of methyl 4-[2-formamido-2-(3-pyridyl)ethyl]-benzoate.

5) To 0.30 g of methyl 4-[2-formamido-2-(3-pyridyl)ethyl]benzoate in 10 ml of methanol-1,4 dioxane (1:1) in solution was added 5 ml of 4% sulfuric acid, and stirred under heating at 60 ° C for three hours, which was then poured into an aqueous saturated solution of sodium hydrogencarbonate to be extracted with ethyl acetate. The organic phase was washed in saturated aqueous sodium chloride solution, and dried over magnesium sulfate, to produce 0.19 g of methyl 4-[2-amino-2-(3-pyridyl)ethyl]benzoate after the evaporation of the solvent.

6) To 0.19 g (0.74 mM) of methyl 4-[2-amino-2-(3-pyridyl)ethyl]benzoate in 10ml of dichloromethane in solution were added triethylamine (0.13 ml, 0.9 mM) and p-chlorobenzenesulfonyl chloride (0.19 g, 0.9 mM), and stirred overnight at room temperature. After completion of the reaction, water was poured into the reaction mixture, followed by extraction of dichloromethane. The organic phase was then washed in saturated aqueous sodium chloride solution and dried over magnesium sulfate, to distill off the solvent. The residue was subjected to chromatography on a silica gel column, which was then eluted with chloroform to yield 0.11 g of methyl 4-[2-(4-chlorobenzenesulfonamido)-2-(3-pyridyl)ethyl]benzoate. The spectrometric data thereof supports the structure of [26] as follows.

$^1$H NMR (CDCl$_3$+CD$_3$OD) δ: 3.05(2H, d J=7.5 Hz), 3.90(3H, s), 4.56(1H, t, J=7.5 Hz), 7.0–7.65(8H, m), 7.81(2H, d, J=8.4 Hz), 8.33(2H, m)

Chemical Formula 26

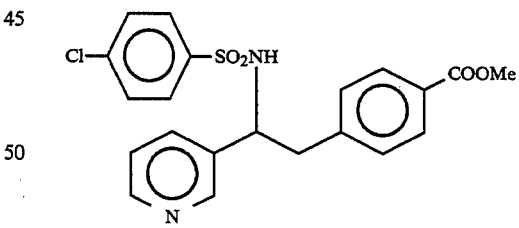

[26]

EXAMPLE 19

To 0.08 g of methyl 4-[2-(4-chlorobenzenesulfonamido)-2-(3-pyridyl)ethyl]benzoate in 10 ml of methanol-1,4 dioxane (1:1 v/v) in solution was added 2 ml of 2N aqueous sodium hydroxide solution and stirred overnight at room temperature. After completion of the reaction, the crystalline deposited was filtered to produce 62 mg of ethyl 4-[2-(4-chlorobenzenesulfonamido)-2-(3-pyridyl)ethyl]benzoic acid. The spectrometric data thereof supports the structure of [27]as follows.

Chemical Formula 27

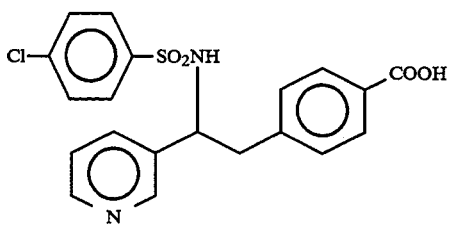

[27]

$^1$H NMR (DMSO-d$_6$) δ: 2.95(2H, d, J=7.5 Hz), 4.52(1H, br. t, J=7.5 Hz), 7.00-7.70(8H, m), 7.76(2H, d, J=8.5 Hz), 8.32(2H, m), 8.60(1H, d, J=8.0 Hz)

EXAMPLE 20

1) p-Tolylacetic acid (10 g) was dissolved in 30 ml of absolute methanol, followed by addition of 10% hydrogen chloride-methanol (10 ml), and stirred overnight at room temperature. The reaction solution was concentrated and dissolved in chloroform, followed by washing in saturated aqueous sodium chloride solution and dried over anhydrous magnesium sulfate, to distill off the solvent. Methyl p-tolylacetate (11 g) was obtained.

2) Methyl p-tolylacetate (11 g) was dissolved in 250 ml of carbon tetrachloride, followed by addition of 11.7 g of N-bromosuccinimide and 0.15 g of benzoyl peroxide, and refluxed under heating for 2.5 hours. The reaction mixture obtained was cooled, followed by filtration and distillation of the solvent, which was then fractionated at 4 mmHg and 142 to 150 ° C. to produce methyl 4-bromomethylphenylacetate (5.3 g).

3) Diisopropylamine (2.8 g) in 50 ml of tetrahydrofuran in solution was cooled to −35 to −40° C., followed by addition of 1.5M n-butyllithium in 118 ml of hexane in solution, and stirred for 30 minutes to produce lithium diisopropylamide. To the solution was added a solution of 4.7 g of 2-(3-pyridyl)-2-(trimethylsiloxy)acetonitrile in dry tetrahydrofuran at −78° C., and stirred at the same temperature for 30 minutes, followed by addition of a solution of 5.3 g of methyl 4-bromomethylphenylacetate in dry tetrahydrofuran at −78° C., and stirred overnight from −78° C. to room temperature. To the reaction mixture was added 1.0M tetra-n-butylammonium fluoride in dry tetrahydrofuran (23 ml) in solution, and stirred at room temperature for four hours. The reaction solution was poured into saturated aqueous sodium chloride solution, followed by the separation of the organic phase. The aqueous phase was extracted with ethyl acetate subsequently. The organic phase was washed in saturated aqueous sodium chloride solution and dried over magnesium sulfate, to distill off the solvent. The residue was subjected to chromatography on a silica gel column, which was then eluted with chloroform to produce 2.3 g of methyl 4-[2-oxo-2-(3-pyridyl)ethyl]phenylacetate.

4) To 13 g of methyl 4-[2-oxo-2-(3-pyridyl)ethyl]phenylacetate was added 8.0 g of ammonium formate, and reacted at 150° C. for four hours. After cooling, water was added, followed by extraction with chloroform. The chloroform phase obtained was washed in saturated aqueous sodium chloride solution and dried over magnesium sulfate, followed by distillation of the solvent, to produce 0.38 g of methyl 4-[2-formamido-2-(3-pyridyl)ethyl]phenylacetate.

5) To 0.38 g of methyl 4-[2-formamido-2-(3-pyridyl)ethyl]phenylacetate in 10 ml of methanol-1,4 dioxane (1:1) in solution was added 5 ml of 4% sulfuric acid, and stirred under heating at 60° C. for one hour, which was then poured into saturated aqueous sodium chloride solution for extraction with ethyl acetate. The ethyl acetate phase obtained was washed in saturated aqueous sodium chloride solution and dried over magnesium sulfate, followed by distillation of the solvent, to produce 0.11 g of methyl 4-[2-amino-2-(3-pyridyl)ethyl]phenylacetate.

6) To 0.11 g of methyl 4-[2-amino-2-(3-pyridyl)ethyl]phenylacetate in 10 ml of dichloromethane were added 0.07 ml of triethylamine (0.07 ml) and 0.11 g of p-chlorobenzenesulfonyl chloride, and stirred overnight at room temperature. After completion of reaction, water was added to the reaction mixture, which was then extracted with dichloromethane, followed by washing in saturated aqueous sodium chloride solution and dried over magnesium sulfate to obtain residue of 0.31 g. The residue was subjected to chromatography on a silica gel column, which was then eluted with chloroform-methanol (10:1 v/v) to produce 0.1 g of methyl 4-[2-(4-chlorobenzenesulfonamido)-2-(3-pyridyl)ethyl]phenylacetate. The spectrometric data thereof supports the structure of [28] as follows.

Chemical Formula 28

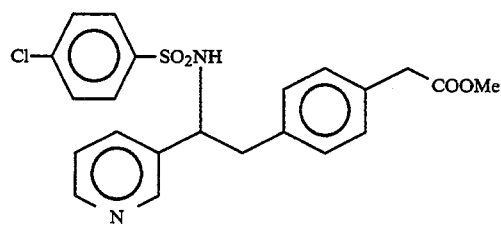

[28]

$^1$H NMR (CDCl$_3$) δ: 2.96(2H, d, J=7.5 Hz), 3.58(2H, s), 3.90(3H, s), 4.56(f1H, dt, J=6.6 Hz, 7.5 Hz), 6.38(1H, d, J=6.6 Hz), 6.85-7.75(11H, m), 8.42(2H, br. s)

EXAMPLE 21

To 0.06 g of methyl 4-[2-(4-chlorobenzenesulfonamido)-2-(3-pyridyl)ethyl]phenylacetate in 10 ml of methanol-1,4 dioxane (1:1) solution was added 2 ml of aqueous 2N sodium hydroxide solution, and stirred overnight at room temperature. After completion of reaction, the solution was neutralized with 2 ml of 2N hydrogen chloride. The crystalline deposited was filtered to produce 49 mg of 4-[2-(4-chlorobenzenesulfonamido)-2-(3-pyridyl)ethyl]phenylacetic acid. The spectrometric data thereof supports the structure of [29] as follows.

Chemical Formula 29

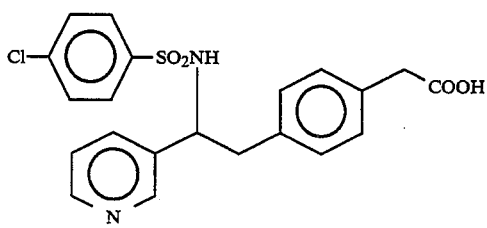

[29]

$^1$H NMR (DMSO-d$_6$) δ: 2.88(2H, d, J=7.9 Hz), 3.52(2H, s), 4.56(1H, br. t, J=7.9 Hz), 6.90–7.80(10H, m), 8.35(2H, m), 8.56(1H, d, J=7.8 Hz)

EXAMPLE 22

1) Ten grams of 4-hydroxybenzyl cyanide was dissolved in 80 ml of methylene chloride, followed by addition of 20 ml of diisopropylethylamine and 9.1 g of chloromethyl methyl ether at 0 C., and stirred overnight at room temperature. The reaction solution was poured into 2N hydrogen chloride, followed by extraction of methylene chloride and washing in saturated aqueous sodium chloride solution, and dried over anhydrous sodium sulfate to obtain residue. The residue was subjected to chromatography on a silica gel column, which was then eluted with chloroform to produce 12.8 g of 4-methoxymethyloxybenzyl cyanide.

2) The solution of 2.3 g of diisopropylamine in 30 ml of dry tetrahydrofuran was cooled to −35 to −40° C., followed by addition of 1.5M n-butyl lithium in 15 ml hexane in solution, and stirred for 30 minutes, to produce lithium diisopropylamide. To the solution was added the solution of 2.0 g of 4-methoxymethyloxybenzyl cyanide in 15 ml of dry tetrahydrofuran at −78° C., and stirred at the same temperature for 30 minutes, followed by addition of 3-picolyl chloride hydrochloride (1.9 g) at −78° C., and stirred overnight to room temperature. The reaction solution was poured into saturated aqueous sodium chloride solution, which was then extracted with ethyl acetate. The ethyl acetate phase was dried over magnesium sulfate, followed by the distillation of the solvent to obtain residue. The residue was subjected to chromatography on a silica gel column, which was then eluted with chloroform-methanol (50:1 v/v) to produce 0.67 g of 2-(4-methoxymethyloxyphenyl)-3-(3-pyridyl)propionitrile.

3) An appropriate amount of Raney nickel was suspended in 30 ml of saturated ammonical methanol solution, followed by addition of 3.81 g of 2-(4-methoxymethyloxyphenyl)-3-(3-pyridyl)propionitrile, and stirred for 72 hours in hydrogen atmosphere of 15 atm. The reaction mixture was filtered and the filtrate was concentrated under reduced pressure. The residue obtained was subjected to chromatography on a silica gel column, which was then eluted with aqueous ammonia-methanol-chloroform (1:10:100 v/v), and from the eluted fraction was obtained 3.27 g of 2-(4-methoxymethyloxyphenyl)-3-(3-pyridyl)propylamine.

4) To the solution of 1.59 g of 2-(4-methoxymethyloxyphenyl)-3-(3-pyridyl)propylamine and 709 mg of triethylamine in 30 ml of methylene chloride was added 1.48 g of P-chlorobenzenesulfonyl chloride, and stirred at room temperature for 30 hours. The reaction mixture was poured into water, and the organic phase was then separated which was extracted from aqueous phase with methylene chloride. The combined organic phases were washed in saturated aqueous sodium chloride solution, and dried over magnesium sulfate, to distill off the solvent. The obtained residue was subjected to chromatography on a silica gel column, and from a fraction eluted with methanol-methylene chloride (5:95 v/v) was obtained 1.23 g of N-[2-(4-methoxymethyloxyphenyl)-3-(3-pyridyl)propyl]-4-chlorobenzenesulfonamide.

5) The portion of 120 mg of 60% sodium hydride were suspended in 10 ml of dimethylformamide, and cooled to 0° C., followed by dropwise addition of 1.22 g of N-[2-(4-methoxymethyloxyphenyl)-3-(3-pyridyl)propyl]-4-chlorobenzenesulfonamide, and then followed by addition of 326 mg of ethyl chlorocarbonate. After stirring at room temperature for 19 hours, the reaction mixture was poured into water. The aqueous phase was extracted with ethyl acetate, and the organic phase was washed in saturated aqueous sodium chloride and dried over magnesium sulfate, to distill off the solvent. The obtained residue was subjected to chromatography on a silica gel column, and from the fraction eluted with methylene chloride was obtained 1.12 g of N-ethoxycarbonyl-N-[2-(4-methoxymethyloxyphenyl)-3-(3-pyridyl)propyl]-4-chlorobenzenesulfonamide.

6) To the solution of 8 ml of the solution of 1.11 g of N-ethoxycarbonyl-N-[2-(4-methoxymethyloxyphenyl)-3-(3-pyridyl)propyl]-4-chlorobenzenesulfonamide in dioxane was added 2 ml of aqueous 6N hydrogen chloride solution, and stirred at room temperature for 7 hours. To the reaction mixture were added water and methylene chloride, followed by further addition of sodium hydrogen carbonate. The organic phase was separated, which was then extracted with ethyl acetate from aqueous phase. The organic phases were combined and washed in saturated aqueous sodium chloride, followed by drying over magnesium sulfate to distill off the solvent under reduced pressure. The obtained residue was subjected to chromatography on a silica gel column, and from the fraction eluted with methanol-methylene chloride (1:99 v/v) was obtained 956 mg of N-ethoxycarbonyl-N-[2-(4-hydroxyphenyl)-3-(3-pyridyl)propyl]-4-chlorobenzenesulfonamide.

7) The solution of N-ethoxycarbonyl-N-[2-(4-hydroxyphenyl)-3-(3-pyridyl)propyl]-4-chlorobenzenesulfonamide (955 mg) in 8 ml of tetrahydrofuran and 5 ml of dimethyl sulfoxide was cooled to 0° C., followed by addition of 1.38 ml of 1.6M n-butyllithium in hexane in solution, and stirred at the same temperature for 30 minutes. Subsequently, saturated aqueous ammonium chloride solution was added to the reaction mixture, followed by separation of the organic layer, which was then extracted with ethyl acetate. The organic phases were combined and washed in saturated aqueous sodium chloride solution, followed by drying over magnesium sulfate, to distill off the solvent. The obtained residue was subjected to chromatography on a silica gel column, and from a fraction eluted with methylene chloride was obtained ethyl 4-[{1-[N-ethoxycarbonyl)-4-chlorobenzenesulfonamide]-3-(3 -pyridyl)}propan-2-yl]phenoxyacetate. The spectrometric data supports the structure of [30] as follows.

Chemical Formula 30

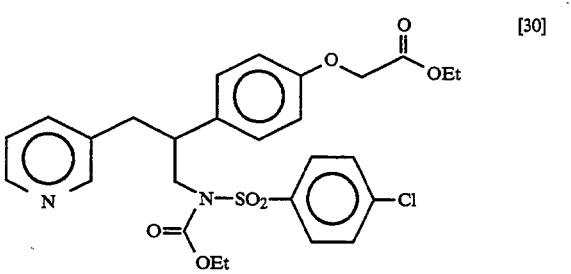

$^1$H NMR (CDCl$_3$) δ: 1.14(3H, t, J=7 Hz), 1.26(3H, t, J=7 Hz), 2.67–3.57(3H, m), 3.77–4.44(6H, m), 4.54(2H, s), 6.52–7.70(10H, m), 7.90–8.47(2H, m)

EXAMPLE 23

Ethyl 4-[{1-[N-ethoxycarbonyl)-4-chlorobenzenesulfonamido]-3-(3-pyridyl)}propan-2-yl]phenoxyacetate (141 mg) was dissolved in 2 ml of ethanol, followed by addition of 1 ml of aqueous 1N sodium hydroxide solution, and stirred at room temperature for one hour. The reaction mixture was concentrated under reduced pressure. To the residue was added 1N hydrogen chloride for neutralization, and the deposited crystalline was filtered to obtain 61 mg of 4-[{1-(4-chlorobenzenesulfonamido)-3-(3-pyridyl)}propan-2-yl]phenoxyacetic acid. The spectrometric data supports the structure of [31] as follows.

Chemical Formula 31

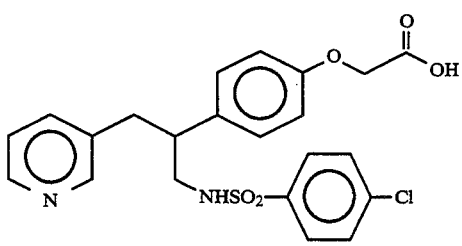

[31]

$^1$H NMR (DMSO-d$_6$) δ: 2.55–3.36(5H, m), 4.50(2H, s), 6.67–7.91 (10H, m), 8.05–8.40(2H, m)

EXAMPLE 24

1) As in Example 22, N-[2-(4-benzyloxyphenyl)-3-(3-pyridyl)propyl]-4-chlorobenzenesulfonamide was obtained from 4-benzyloxybenzyl cyanide.

2) The N-[2-(4-benzyloxyphenyl)-3-(3-pyridyl)-propyl]-4-chlorobenzenesulfonamide (170 mg) was dissolved in 10 ml of ethanol, followed by addition of 0.2 g of 10% palladium carbon, and stirred for catalytic reduction via hydrogen at 55° C. overnight, to obtain 82 mg of N-[2-(4-hydroxyphenyl)-3-(3-pyridyl)propyl]-4-chlorobenzenesulfonamide.

3) A portion of 53 mg of N-[2-(4-hydroxyphenyl)-3-(3-pyridyl)propyl]-4-chlorobenzenesulfonamide and 78 mg of triethylamine were dissolved in 8 ml of tetrahydrofuran, followed by addition of 25 mg of ethyl chlorocarbonate dissolved in 1 ml of tetrahydrofuran, and stirred at room temperature for 10 minutes. The crystalline deposited was filtered, and the filtrate was then concentrated under reduced pressure. The residue was subjected to chromatography on a silica gel column, and from a fraction eluted with methanol-methylene chloride (5:95 v/v) was obtained 53 mg of N-[2-(4-ethoxycarbonyloxyphenyl)-3-(3-pyridyl)}propyl]-4-chlorobenzenesulfonamide. The spectrometric data supports the structure of [32] as follows.

Chemical Formula 32

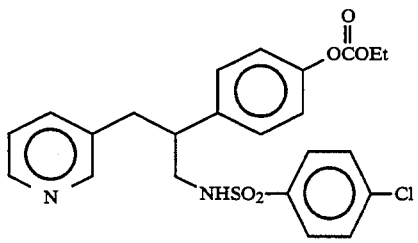

[32]

$^1$H NMR (CDCl$_3$) δ: 1.37(3H, t, J=7.5 Hz), 2.77–3.40(5H, m), 4.28(2H, q, J=7.5 Hz), 5.16–5.45(1H, m), 6.95–7.97(10H, m), 8.08–8.53(2H, m)

EXAMPLE 25

1) 4-Cresol (59 g) was dissolved in 500 ml of methylene chloride, followed by addition of 238 ml of diisopropylethylamine and 66 g of chloromethyl methyl ether, and stirred at room temperature for two nights. The reaction solution was poured into water, which was then extracted with methylene chloride. After washing in 2N hydrogen chloride and then washing in saturated aqueous sodium chloride, the extract was dried over anhydrous sodium sulfate to yield residue. The residue was subjected to chromatography which was eluted with chloroform, to obtain 4-tolyl methoxymethyl ether.

2) 4-Tolyl methoxymethyl ether (15.2 g) was dissolved in 100 ml of carbon tetrachloride, followed by addition of 19.8 g of N-bromosuccinimide and 0.24 g of benzoyl peroxide, and refluxed for 1.5 hours. The resulting reaction mixture was cooled, and subsequently filtered to distill off the solvent to obtain bromomethylphenyl methoxymethyl ether (23 g).

3) The solution of 11.1 g of diisopropylamine in 150 ml of dry tetrahydrofuran was cooled to −35° C. to −40° C., followed by addition of 67 ml of the solution of 1.5M n-butyllithium hexane, and stirred for 30 minutes to produce lithium diisopropylamide. To the solution was added 11.8 g of 3-pyridine acetonitrile in 100 ml of dry tetrahydrofuran in solution, and stirred at the same temperature for 30 minutes, followed by addition of 23 g of bromomethylphenyl methoxymethyl ether at −78° C., which was then stirred from −78° C. to room temperature overnight. The reaction solution was poured into saturated aqueous sodium chloride, which was extracted with ethyl acetate. The ethyl acetate phase was dried over sodium sulfate, and the solvent was distilled off to obtain 24.5 g of the residue. The residue was subjected to chromatography on a silica gel column, which was then eluted with chloroform, to obtain 8.0 g of 3-(4-methoxymethyloxyphenyl)-2-(3-pyridyl)propionitrile.

4) An appropriate amount of Raney nickel was suspended in 30 ml of saturated solution of ammonium and methanol, followed by addition of 5.75 g of 3-(4-methoxymethyloxyphenyl)-2-(3-pyridyl)propionitrile, and stirred for 64 hours under hydrogen atmosphere of 15 atm. The reaction mixture was filtered and the filtrate was concentrated under reduced pressure. The residue obtained was subjected to chromatography on a silica gel column, which was then eluted with aqueous ammonia-methanol-chloroform (1:10:100 v/v), and from the eluted fraction was obtained 4.98 g of 3-(4-methoxymethyloxyphenyl)-2-(3-pyridyl)propylamine.

5) To the solution of 4.98 g of 3-(4-methoxymethyloxyphenyl)-2-(3-pyridyl)propylamine and 100 ml of the solution of 2.22 g of triethylamine in methylene chloride was added 4.63 g of chlorobenzenesulfonyl chloride, and stirred at room temperature for four hours. The reaction mixture was poured into water, and the organic phase was separated which was then extracted with methylene chloride from aqueous phase. The combined organic phases were washed in saturated aqueous sodium chloride, and dried over magnesium sulfate, to distill off the solvent. The obtained residue was subjected to chromatography on a silica gel column, and from the fraction eluted with methanol-methylene chloride (5:95 v/v) was obtained 3.79 g of N-[3-(4-methoxymethyloxyphenyl)-2-(3-pyridyl)propyl]-4-chlorobenzene sulfonamide.

6) A portion of 144 mg of 60% sodium hydride were suspended in 15 ml of dimethylformamide and cooled to 0° C., followed by dropwise addition of 1.34 g of N-[3-(4-methoxymethyloxyphenyl)-2-(3-pyridyl)propyl]-4-chlorobenzene sulfonamide, and then followed by addition of 391 mg of ethyl chlorocarbonate. After stirring at room temperature for four hours, the reaction mixture was poured into water. The aqueous phase was extracted with ethyl acetate, and the organic phase was washed in saturated aqueous sodium chloride and dried over magnesium sulfate, to distill off the solvent. The obtained residue was subjected to chromatography on a silica gel column, and from a fraction eluted with methylene chloride was obtained 1.49 g of N-ethoxycarbonyl-N-[3-(4-methoxymethyloxyphenyl)-2-(3-pyridyl)propyl]-4-chlorobenzenesulfonamide.

7) To 12 ml of the solution of 1.48 g of N-ethoxycarbonyl-N-[3-(4-methoxymethyloxyphenyl)-2-(3-pyridyl)propyl]-4-chlorobenzenesulfonamide in dioxane was added 4 ml of aqueous 6N hydrogen chloride solution, and stirred at room temperature for eight hours. To the reaction mixture were added water and methylene chloride, followed by further addition of sodium hydrogencarbonate.

The organic phase was separated, which was then extracted with ethyl acetate from aqueous phase. The organic phases were combined and washed in saturated aqueous sodium chloride, followed by drying over magnesium sulfate to distill off the solvent under reduced pressure. The obtained residue was subjected to chromatography on a silica gel column, and from a fraction eluted with methanol-methylene chloride (1:99 v/v) was obtained 975 mg of N-ethoxycarbonyl-N-[3-(4-hydroxyphenyl)-2-(3-pyridyl)}propyl]-4-chlorobenzenesulfonamido.

8) The solution of 633 mg of N-ethoxycarbonyl-N-[3-(4-hydroxyphenyl)-2-(3-pyridyl)}propyl]-4-chlorobenzene sulfonamide in 4 ml of tetrahydrofuran and 3 ml of dimethyl sulfoxide was cooled to 0° C., followed by dropwise addition of 1.0 ml of the solution of 1.6M n-butyl lithium in hexane, and stirred at the same temperature for 30 minutes, followed by dropwise addition of 0.18 ml of ethyl bromoacetate, and stirred at room temperature for 20 hours. To the reaction mixture was added aqueous saturated ammonium chloride solution. The organic phase was separated, which was then extracted with ethyl acetate from the aqueous phase. The organic phases were combined and washed in saturated aqueous sodium chloride, and dried over magnesium sulfate to distill off the solvent under reduced pressure. The obtained residue was subjected to chromatography on a silica gel column, and from a fraction eluted with methylene chloride was obtained 324 mg of ethyl 4-[(3-(N-ethoxycarbonyl)-4-chlorobenzenesulfonamide]-2-(3-pyridyl))}propyl]phenoxyacetate. The spectrometric data supports the structure of [33] as follows.

Chemical Formula 33

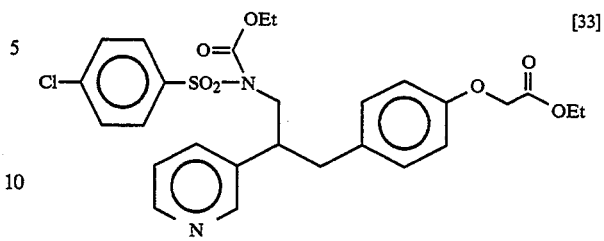

$^1$H NMR (CDCl$_3$) δ: 1.11(3H, t, J=7 Hz), 1.24(3H, t, J=7 Hz), 2.68–3.68(3H, m), 3.78–4.44(6H, m), 4.50(2H, s), 6.54–7.71(10H, m), 8.21–8.53(2H, m)

EXAMPLE 26

Ethyl 4-[(3-(N-ethoxycarbonyl)-4-chlorobenzenesulfonamido]-2-(3-pyridyl))}propyl]phenoxyacetate (181 mg) was dissolved in 2 ml of ethanol, followed by addition of 2 ml of aqueous 1N sodium hydroxide solution, and stirred at room temperature for 24 hours. The reaction mixture was concentrated under reduced pressure. To the residue was added 1N hydrogen chloride for neutralization, and the deposited crystalline was filtered to obtain 89 mg of [3-(4-chlorobenzenesulfonamido)-2-(3-pyridyl))}propyl]phenoxyacetic acid. The spectrometric data supports the structure of [34] as follows.

Chemical Formula 34

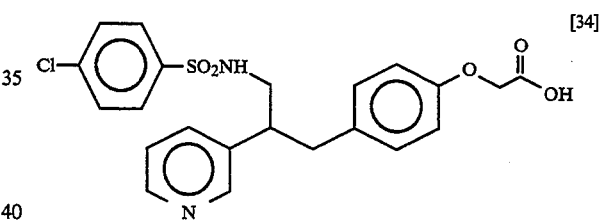

$^1$H NMR (CDCl$_3$-CD$_3$OD) δ: 2.64–3.03(5H, m), 4.48(2H, s), 6.48–7.79(10H, m), 7.95–8.42(2H, m)

EXAMPLE 27

1) To 10 ml solution of the N-[3-(4-methoxymethyloxyphenyl)-2-(3-pyridyl)propyl]-4-chlorobenzene sulfonamide (0.72 g) obtained as in Example 25 5) in 1,4 dioxane was added 6N hydrogen chloride, and stirred at 80° C. for 10 minutes. To the reaction mixture was added water, followed by adjustment of the solution to pH 4, which was then extracted with ethyl acetate. After washing in saturated aqueous sodium chloride solution, dehydration with magnesium sulfate yielded 0.6 g of residue. The residue was subjected to chromatography on silica gel, which was then eluted with chloroform-methanol (50:1 v/v), to obtain 0.52 g of N-[3-(4-hydroxyphenyl)-2-(3-pyridyl)propyl]-4-chlorobenzenesulfonamide.

2) N-[3-(4-hydroxyphenyl)-2-(3-pyridyl)propyl]-4-chlorobenzenesulfonamide (54.5 mg) and 15.1 mg of triethylamine were dissolved in 3 ml of methylene chloride, followed by addition of 16.2 mg of ethyl chlorocarbonate dissolved in 1 ml of methylene chloride, and stirred at room temperature for 15 hours. To the reaction mixture was added water, and the organic phase was separated which was then extracted with methylene chloride. The organic phases were combined and washed in water, followed by drying over magnesium sulfate, to distill off the solvent. The obtained residue was subjected to chromatography on a silica gel column, and from a fraction eluted with methanol-methylene chloride (5:95 v/v) was obtained 47.4 mg of N-[3-(4-ethoxycarbonylphenyl)-2-(3-pyridyl)}propyl]-4-chlorobenzene sulfonamide. The spectrometric data supports the structure of [35] as follows.

Chemical Formula 35

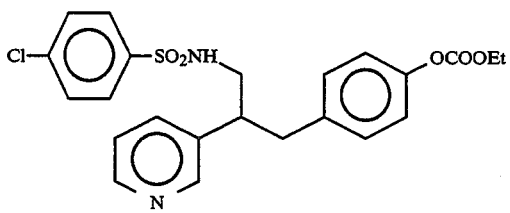

[35]

$^1$H NMR (CDCl$_3$) δ: 1.38(3H, t, J=7.5 Hz), 2.83–3.47(5H, m), 4.35(2H, q, J=7.5 Hz), 6.13(1H, br. t, J=5 Hz), 7.00–7.88(10H, m), 8.25–8.53(2H, m)

EXAMPLE 28

1-(3-Pyridyl)-2-propen-1-ol (1.36 g), methyl p-bromobenzoate (1.44 g) and palladium acetate II (0.02 g) were dissolved in 30 ml of N,N-dimethylformamide, and stirred under heating at 120° C. overnight. The obtained reaction mixture was concentrated, to which was poured water and extracted with ethyl acetate. The extract with ethyl acetate was washed in saturated aqueous sodium chloride solution and dried over magnesium sulfate. The residue was subjected to chromatography on a silica gel column, which was eluted with chloroform-methanol (20:1 v/v), to obtain 1.25 g of methyl 4-[3-oxo-3-(3-pyridyl)propyl]benzoate.

2) Methyl 4-[3-oxo-3-(3-pyridyl)propyl]benzoate (1.25 g) and ammonium formate (8.8 g) were stirred under heating at 150° C. After cooling, water was poured into the mixture, which was then extracted with chloroform. The obtained extract was dried over magnesium sulfate. The residue was subjected to chromatography on a silica gel column, which was eluted with chloroform-methanol (20:1 v/v) to obtain 0.62 g of methyl 4-[3-formamide-3-(3-pyridyl)propyl]benzoate.

3) To 10 ml of the solution of 0.62 g of methyl 4-[3-formamido-3-(3-pyridyl)propyl]benzoate methanol-1,4 dioxane (1:1) was added 5 ml of 4% sulfuric acid, and stirred under heating at 60° C. overnight, which was then poured into saturated aqueous sodium hydrogencarbonate solution to be extracted with ethyl acetate. The obtained ethyl acetate phase was washed in saturated aqueous sodium chloride and dried over magnesium sulfate, to distill off the solvent, so that 0.35 g of methyl 4-[3-amino-3-(3-pyridyl)propyl]benzoate was yielded.

4) To 10 ml of the solution of 0.35 g of methyl 4-[3-amino-3-(3-pyridyl)propyl]benzoate in dichloromethane were added 0.22 ml of triethylamine and 0.33 g of p-chlorobenzene sulfonylchloride, and stirred at room temperature overnight. After completion of the reaction, the reaction mixture was poured into water, which was then extracted with dichloromethane, washed in saturated aqueous sodium chloride and dried over magnesium sulfate. The residue was subjected to chromatography on a silica gel column, to obtain 0.34 g of methyl 4-[3-(4-chlorobenzenesulfonamido)-3-(3-pyridyl)propyl]benzoate. The spectrometric data supports the structure of [36] as follows.

Chemical Formula 36

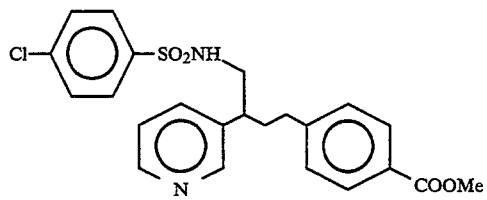

[36]

$^1$H NMR (CDCl$_3$) δ: 8.46(1H, dd, J=1.8 Hz, 4.6 Hz), 8.30(1H, br. d, J=1.8 Hz), 7.96(2H, d. J=7.0 Hz), 7.32(8H, m), 5.44(1H, d. J=7.5 Hz), 4.35(1H, dt, J=7.3, 7.5), 3.91(3H, s), 2.62(2H, m), 2.12(2H, m)

EXAMPLE 29

To 20 ml of the solution of 0.14 g of methyl 4-[3-(4-chlorobenzenesulfonamido)-3-(3-pyridyl)propyl}benzoate in methanol-1,4 dioxane (1:1) was added 5 ml of aqueous 2N sodium hydroxide solution, and stirred at room temperature overnight. After completion of the reaction followed by neutralization with 5 ml of 2N hydrogen chloride, the crystalline deposited was filtered to obtain 72 mg of 4-[3-(4-chlorobenzenesulfonamido)-3-(3-pyridyl)propyl]benzoic acid. The spectrometric data supports the structure of [37] as follows.

Chemical Formula 37

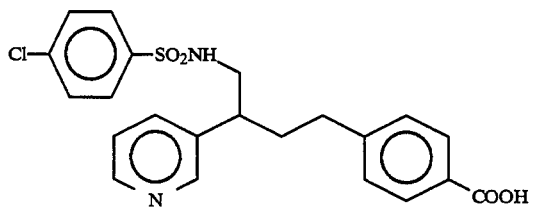

[37]

$^1$H NMR (DMSO-d$_6$) δ: 8.81(d, 1H, J=7.8 Hz), 8.62(m, 2H), 7.52(9H, m), 4.47(dt, 1H, J=7.5 Hz, 7.5 Hz), 2.00(m, 2H)

EXAMPLE 30

1) p-Hydroxybenzaldehyde (4.88 g), bromoacetic acid (6.68 g) and potassium carbonate (5.53 g) were suspended in 100 ml of acetone, and refluxed for 15 hours. After the solvent was distilled off under reduced pressure, water was added followed by extraction with methylene chloride. The organic phase was washed in saturated aqueous sodium chloride, and dried over magnesium sulfate. After distillation of the solvent under reduced pressure, 8.32 g of ethyl 4-formylphenoxyacetate was obtained.

2) In argon atmosphere, 15.19 g of dimethyl methylphosphonate was dissolved in 170 ml of dry tetrahydrofuran, followed by dropwise addition of 1.55M n-butyl lithium solution in hexane at −78° C., which was then stirred at the same temperature for 80 minutes. Methyl nicotinate (16.79 g) dissolved in 50 ml of dry tetrahydrofuran was added dropwise and stirred at −78° C. for 20 hours, followed by addition of water. The organic solvent was distilled off under reduced pressure, which was extracted with methylene chloride. Alternatively, 2N hydrogen chloride was added to aqueous phase for neutralization, which was then extracted with ethyl acetate. The organic phase was washed in saturated aqueous sodium chloride, and dried over magnesium sulfate, to distill off the solvent under reduced pressure. The obtained residue was subjected to chromatography on a silica gel column, and from a fraction eluted with methanol-methylene chloride (5:95 v/v), 19.30 g of dimethyl 2-oxo-2-(3-pyridyl)ethylphosphonate was obtained.

3) In nitrogen atmosphere, 0.52 g of sodium hydride (containing mineral oil at 60%) was washed in hexane, which was then suspended in 30 ml of dry tetrahydrofuran. After cooling to 0° C., 2.75 g of dimethyl 2-oxo-2-(3-pyridyl)ethylphosphonate dissolved in 10 ml of anhydrous tetrahydrofuran was added and stirred at room temperature for 30 minutes, followed by addition of 2.08 g of ethyl 4-formylphenoxyacetate, which was then refluxed for 18 hours. After addition of saturated aqueous sodium chloride, the organic phase was separated which was subsequently extracted with ethyl acetate from aqueous phase. Thereafter, the organic phases combined were washed in saturated aqueous sodium chloride, dried over magnesium sulfate, and then the solvent was distilled off. The residue obtained was subjected to chromatography on a silica gel column, and from a fraction eluted with methanol-methylene chloride (2:98 v/v) was obtained 1.79 g of ethyl 4-[3-oxo-3-(3-pyridyl)-1-propenyl]phenoxyacetate.

4) Ethyl 4-[3-oxo-3-(3-pyridyl)-1-propenyl]phenoxyacetate (3.85 g) and 1.15 g of 10% Pd—C were suspended in 300 ml of ethanol, and stirred in hydrogen atmosphere at ambient temperature and pressure for three hours. The reaction mixture was filtered, and the filtrate was evaporated under reduced pressure. The residue obtained was subjected to chromatography on a silica gel column, and from a fraction eluted with methylene chloride was obtained 1.95 g of ethyl 4-[3-oxo-3-(3-pyridyl)propyl]phenoxyacetate.

5) 1.95 g of ethyl 4-[3-oxo-3-(3-pyridyl)propyl]phenoxyacetate and 5.00 g of ammonium formate were stirred at 165° C. for 1.5 hours. To the reaction mixture was added aqueous sodium hydrogencarbonate solution, which was then extracted with ethyl acetate, and the organic phases combined were washed in saturated aqueous sodium chloride, dried over magnesium sulfate, and the solvent was then distilled off. The obtained residue was subjected to chromatography on a silica gel column, and from a fraction eluted with methanol-methylene chloride (5:95 v/v) was obtained 0.95 g of ethyl 4-[3-formamido-3-(3-pyridyl)propyl]phenoxyacetate.

6) In a mixed solvent of 4 ml of ethanol, 4 ml of tetrahydrofuran, and 4 ml of water was dissolved 150 mg of ethyl 4-[3-formamido-3-(3-pyridyl)propyl]phenoxyacetate, followed by addition of 0.15 ml of conc. sulfuric acid, which was then heated to 60° C. and stirred for 12 hours. After completion of the reaction, the solvent was distilled off under reduced pressure, followed by addition of methanol-methylene chloride (5:95 v/v) and water. While stirring, the property of the solution was adjusted to weak alkalinity with gradual addition of saturated aqueous sodium hydrogencarbonate solution. After separation of the organic phase, which was then extracted with methanol-methylene chloride (5:95 v/v) from the aqueous phase and washed in saturated aqueous sodium chloride followed by drying over magnesium sulfate and distillation of the solvent, 50 mg of ethyl 4-[3-amino-3-(3-pyridyl)propyl]phenoxyacetate was obtained.

7) Ethyl 4-[3-amino-3-(3-pyridyl)propyl]phenoxyacetate (50 mg) and 30 mg of triethylamine were dissolved in 10 ml of methylene chloride, followed by addition of 50 mg of p-chlorobenzene sulfonylchloride, and stirred at room temperature for 2.5 hours. To the reaction mixture was added water, and the organic phase was then separated which was extracted with methanol-methylene chloride (5:95 v/v) from the aqueous phase. The organic phases were combined and washed in saturated aqueous sodium chloride followed by drying over magnesium sulfate and distillation of the solvent. The obtained residue was subjected to chromatography on a silica gel column, and from a fraction eluted with methanol-methylene chloride (5:95 v/v) was obtained 22 mg of ethyl 4-[3-(4-chlorobenzenesulfonamido)-3-( 3-pyridyl)propyl]phenoxyacetate. The spectrometric data supports the structure of [38] as follows.

Chemical Formula 38

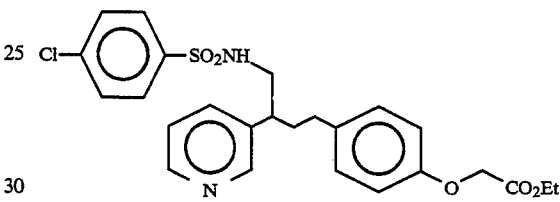

$^1$H NMR (CDCl$_3$) δ: 1.30(3H, t, J=7 Hz), 2.50(2H, t, J=7 Hz), 4.27(2H, q, J=7 Hz), 4.60(2H, s), 5.53(1H, d, J=7 Hz), 6.65–7.65(10H, m), 8.23–8.50(2H, m)

EXAMPLE 31

In a mixed solvent of 2 ml of ethanol and 2 ml of tetrahydrofuran was dissolved 21.8 mg of ethyl 4-[3-(4-chlorobenzenesulfonamido)-3-(3-pyridyl)propyl]phenoxyacetate, followed by addition of 0.25 ml of aqueous 2N sodium hydroxide solution, and stirred at room temperature for 30 minutes. The reaction mixture was concentrated under reduced pressure, which was then neutralized with 2N hydrogen chloride. The crystalline deposited was filtered and washed in water followed by drying, to obtain 4.0 mg of 4-[3-(4-chlorobenzenesulfonamido)-3-(3-pyridyl)propyl]phenoxyacetic acid. The spectrometric data thereof supports the structure of [39] as follows.

Chemical Formula 39

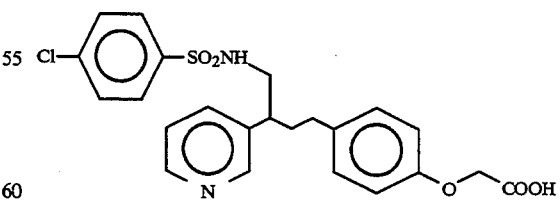

$^1$H NMR (DMSO-d$_6$) δ: 4.54(2H, s), 6.65–7.82(10H, m), 8.23–8.65(2H, m)

EXAMPLE 32

1) p-Tolyl methoxymethyl ether (3.05 g), N-bromosuccinimide (3.92 g) and benzoyl peroxide (0.02 g) were dissolved in 80 ml of carbon tetrachloride, followed by reflux for five hours. After completion of the reaction, the crystalline deposited was filtered. The filtrate was concentrated under reduced pressure to quantitatively obtain 4-bromomethylphenyl methoxymethyl ether. The bromo compound was used without further purification.

2) In argon atmosphere, 2.02 g of diisopropylamine was dissolved in 50 ml of dry tetrahydrofuran, followed by dropwise addition of the solution of 12.5 ml of 1.55M n-butyl lithium in hexane at −20° C., which was then stirred at the same temperature for five minutes and cooled subsequently. 2-(3-pyridyl)-2-(trimethylsiloxy)acetonitrile (4.13 g) dissolved in 20 ml of dry tetrahydrofuran was added dropwise. After stirring at the same temperature for one hour, the reaction mixture was dissolved in 10 ml of tetrahydrofuran. 4-Bromomethylphenyl methoxymethyl ether (4.48 g) was added dropwise, and the temperature was gradually increased from −78° C. to room temperature, followed by stirring overnight. The 20.0 ml of the solution of 1.0M tetra-n-butylammonium fluoride of tetrahydrofuran was added and stirred for 3.5 hours. To the reaction mixture was added saturated aqueous sodium chloride solution, and the organic phase was separated which was then extracted with ethyl acetate from aqueous phase. The organic phases were combined and washed in aqueous sodium Chloride, dried over magnesium sulfate. Then, the solvent was distilled off under reduced pressure. The obtained residue was subjected to chromatography on a silica gel column, and from a fraction eluted with methanol-methylene chloride (2:98 v/v) was obtained 2.30 g of 2-(4-methoxymethyloxyphenyl)-1-(3-pyridyl)ethanone.

3) In argon atmosphere, 0.27 g of sodium was added to 20 ml of dry ethanol, and stirred until the metal piece was solubilized. To the solution was added 0.76 g of diethyl cyanomethyl phosphonate dissolved in 10 ml of dry ethanol, followed by stirring for 15 minutes. Then, 2.73 g of 2-(4-methoxymethyloxyphenyl)-1-(3-pyridyl)ethanone dissolved in 10 ml of dry ethanol was added and refluxed overnight. After completion of the reaction, the solvent was distilled off under reduced pressure, followed by addition of water, which was then extracted with methylene chloride. The organic phase was washed in saturated aqueous sodium chloride and the solvent was distilled off under reduced pressure. The obtained residue was subjected to chromatography on a silica gel column. From a fraction eluted with methanol-methylene chloride (5:95 v/v) was obtained 2.18 g of a mixture of isomers as the products from Wittig-Horner-Emmons reaction.

4) An appropriate amount of Raney nickel was suspended in 15 ml of saturated solution of ammonium and methanol, followed by addition of 0.37 g of the compound (3), and stirred for 40 hours in hydrogen atmosphere of 15 atm. The reaction mixture was filtered, and the filtrate was concentrated under reduced pressure. The residue obtained was subjected to preparative TLC on a silica gel column, which was then developed with aqueous ammonia-methanol-chloroform (1:10:100 v/v) . From a band of Rf 0.32 to 0.58 was obtained 0.21 g of 4-(4-methoxymethyloxyphenyl)-3-(3-pyridyl)butylamine.

5) To the solution of 0.72 g of 4-(4-methoxymethyloxyphenyl)-3-(3-pyridyl)butylamine and 0.27 g of triethylamine in methylene chloride, after cooling at 0° C., was added 0.51 g of chlorobenzene sulfonylchloride, and stirred at room temperature for five hours. To the reaction mixture was added water which was then adjusted to weak acidity with 2N hydrogen chloride, and the organic phase was separated which was then extracted from aqueous phase with methylene chloride. The combined organic phases were washed in saturated aqueous sodium chloride solution, and dried over magnesium sulfate, to distill off the solvent. The obtained residue was subjected to chromatography on a silica gel column, and from a fraction eluted with methanol-methylene chloride (5:95 v/v) was obtained 1.02 g of N-[4-(4-methoxymethyloxyphenyl)-3-(3-pyridyl)butyl]-4-chlorobenzenesulfonamide.

6) In argon atmosphere, 329 mg of N-[4-(4-methoxymethyloxyphenyl)-3-(3-pyridyl)butyl]-4-chlorobenzene sulfonamide was dissolved in 12 ml of dry tetrahydrofuran, and cooled to 0° C., followed by addition of 0.67 ml of the solution of 1.55M n-butyl lithium in hexane, which was then stirred for 30 minutes. At the same temperature, 116 mg of ethyl chlorocarbonate dissolved in 3 ml of dry tetrahydrofuran was added dropwise and stirred at room temperature for 24 hours. To the reaction mixture was added saturated aqueous sodium chloride, and the organic phase was separated which was then extracted with ethyl acetate. The organic phases combined were washed in saturated aqueous sodium chloride and dried over magnesium sulfate, so the solvent was distilled off under reduced pressure. The obtained residue was subjected to preparative silica gel TLC which was then developed with methanol-methylene chloride (4:96 v/v) to obtain 204 mg of N-ethoxycarbonyl-N-[4-(4-methoxymethyloxyphenyl)-3-(3-pyridyl)butyl]-4-chlorobenzene sulfonamide from a band of 0.36 to 0.53.

7) In argon atmosphere, 0.54 g of N-ethoxycarbonyl-N-[4-(4-methoxymethyloxyphenyl)-3-(3-pyridyl)butyl]-4-chlorobenzene sulfonamide was dissolved in 15 ml of methanol, followed by addition of 1 ml of 6N hydrogen chloride, and stirred at 60 ° C. for 45 minutes. After completion of the reaction, the solvent was distilled off under reduced pressure, followed by addition of methylene chloride and further by addition of saturated aqueous sodium hydrogencarbonate so that the resulting mixture became weak alkaline. The organic phase was separated, which was then extracted with methylene chloride. The organic phases combined were washed in saturated aqueous sodium chloride and dried over magnesium sulfate. After the evaporation of the solvent, 0.47 g of N-ethoxycarbonyl-N-[4-(4-hydroxyphenyl)-3-(3-pyridyl)butyl]-4-chlorobenzenesulfonamide was produced.

8) N-ethoxycarbonyl-N-[4-(4-hydroxyphenyl)-3-(3-pyridyl)butyl]-4-chlorobenzenesulfonamide (0.47 g) was dissolved in 10 ml of dry tetrahydrofuran and cooled to 0° C., followed by dropwise addition of 0.74 ml of the solution of 1.55M n-butyllithium in hexane, which was then stirred at the same temperature for two hours. Then, 0.18 g of ethyl bromoacetate dissolved in 5 ml of dry tetrahydrofuran was added, followed by addition of 1 ml of dimethyl sulfoxide, for stirring at room temperature for 22 hours. To the reaction mixture was added saturated aqueous sodium chloride, and the organic phase was separated which was then extracted with ethyl acetate. The organic phases combined were washed in saturated aqueous sodium chloride and dried over magnesium sulfate, so the solvent was distilled off under reduced pressure, to obtain 0.23 g of ethyl 4-{4-(N-ethoxycarbonyl-4-chlorobenzenesulfonamido)-2-(3- pyridyl)butyl]}phenoxyacetate. The spectrometric data supports the structure of [40] as follows.

Chemical Formula 40

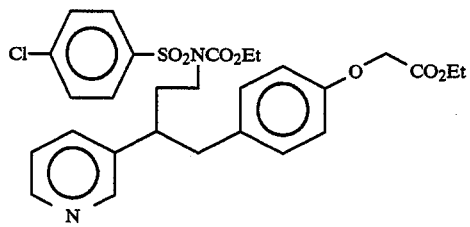

$^1$H NMR (CDCl$_3$) δ: 1.10(3H, t, J=7 Hz) 1.23(3H, t, J=7 Hz), 1.66–2.37(2H, m), 2.60–3.23(3H, m), 3.43–4.40(6H, m), 4.49(2H, s), 6.50–7.90(10H, m), 8.07–8.50(2H, m)

EXAMPLE 33

Ethyl 4-{4-(N-ethoxycarbonyl-4-chlorobenzenesulfonamido)-2-(3-pyridyl)butyl]}phenoxyacetate (0.20 g) was dissolved in 5 ml of ethanol, followed by addition of 1 ml of aqueous 2N sodium hydroxide solution, and stirred at room temperature for 21 hours. The solvent was concentrated under reduced pressure, and the resulting mixture was adjusted to weak acidity with 2N hydrogen chloride, to obtain 0.16 g of 4-{4-(4-chlorobenzenesulfonamido)-2-(3-pyridyl)butyl]} phenoxyacetic acid. The spectrometric data supports the structure of [41] as follows.

Chemical Formula 41

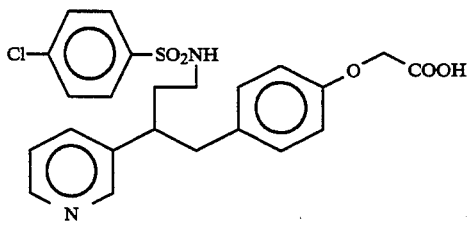

$^1$H NMR (DMSO-d$_6$) δ: 4.58(2H, s), 6.60–7.10(4H, m), 7.34–8.10(6H, m), 8.30–8.50(2H, m)

EXAMPLE 34

1) Pyridine-3-aldehyde (44.4 g), trimethylsilyl cyanide (47.5 g) and zinc iodide (0.01 g) were mixed together and stirred under heating at 90° C. for 1.5 hours. The reaction mixture obtained was fractionated at 5 mmHg and 122 to 132 °C., to obtain 39.8 g of 2-(3-pyridyl)-2-(trimethylsiloxy)acetonitrile.

2) Methyl p-toluylate acid (9.3 g) was dissolved in 200 ml of carbon tetrachloride, followed by addition of 12.2 g of N-bromosuccinimide and 0.15 g of benzoyl peroxide, and stirred under heating overnight. The reaction mixture obtained was cooled and subsequently filtered, to distill off the solvent under reduced pressure, to obtain 13.5 g of methyl 4-bromomethylbenzoate.

3) The 60 ml of the solution of 4.5 g of diisopropylamine in dry tetrahydrofuran was cooled to −30° to −40° C., followed by addition of 30 ml of the solution of 1.6M n-butyl lithium in hexane, and stirred for 30 minutes to produce lithium diisopropylamide.

To the solution was added 2-(3-pyridyl)-2-(trimethylsiloxy)acetonitrile in dry tetrahydrofuran and stirred at the same temperature for 20 minutes. The solution of methyl 4-bromomethylbenzoate in tetrahydrofuran was added to the resulting solution at −78° C., which was then stirred overnight from −78° C. to room temperature.

To the reaction mixture obtained was added the 40 ml of the solution of 1.0M tetra-n-butylammonium fluoride in dry tetrahydrofuran, and stirred at room temperature for 3.5 hours. The reaction solution was poured into saturated aqueous sodium chloride solution, and the organic phase was separated. Thereafter, the aqueous phase was extracted with ethyl acetate.

The organic phases combined were washed in saturated aqueous sodium chloride and dried over magnesium sulfate, to distill off the solvent. The residue was subjected to chromatography on a silica gel column, and the fraction eluted with chloroform-methanol (50:1 v/v) was recrystallized in n-hexane-chloroform, to obtain 3.0 g of methyl 4-[2-oxo-2-(3-pyridyl)ethyl]benzoate.

4) In nitrogen atmosphere, methyl 4-[2-oxo-2-(3-pyridyl)ethyl]benzoate benzoate (2.55 g) was dissolved in 50 ml of dry tetrahydrofuran, to which was added 1.52 g of lithium aluminium hydride suspended in 40 ml of dry tetrahydrofuran, and stirred at 50° C. for 30 minutes.

The reaction mixture was poured into aqueous 2N sodium hydroxide solution, which was extracted with ethyl acetate, followed by washing in saturated aqueous sodium chloride solution and drying over anhydrous magnesium sulfate. Then, the solvent was distilled off under reduced pressure, and the residue obtained was subjected to chromatography on a silica gel column. From a fraction eluted with chloroform-methanol(9:1 v/v) was obtained 1.89 g of 4-[2-hydroxy-2-(3-pyridyl)ethyl]benzyl alcohol.

5) 4-[2-Hydroxy-2-(3-pyridyl)ethyl]benzyl alcohol (1.89 g) was dissolved in 50 ml of acetone, followed by addition of 5.67 g of activated manganese dioxide, and stirred for 15 hours. The reaction mixture was filtered, and the solution in the filtrate was condensed under reduced pressure.

The residue obtained was subjected to chromatography on a silica gel column, and from a fraction eluted with chloroform-methanol(10:1v/v) was obtained 1.34 g of 4-[2-hydroxy-2-(3-pyridyl)ethyl]benzaldehyde.

6) 4-[2-Hydroxy-2-(3-pyridyl)ethyl]benzaldehyde (1.34 g) and (carboethoxyethylidene)triphenylphosphorane (4.28 g) were dissolved in 50 ml of chloroform, and stirred for 1.5 hours, and the solvent was distilled off under reduced pressure. The residue obtained was subjected to chromatography on a silica gel column, and from a fraction eluted with chloroform-methanol(10:1v/v) was obtained 1.84 g of ethyl 4-[2-hydroxy-2-(3-pyridyl)ethyl]-α-methylcinnamate.

7) Ethyl 4-[2-hydroxy-2-(3-pyridyl)ethyl]-α-methylcinnamate (1.84 g) was dissolved in 60 ml of acetone, followed by dropwise addition of 2.27 g of 2.67M Jones Reagent, and stirred for 30 minutes. After addition of 2 ml of isopropanol, the resulting mixture was concentrated under reduced pressure, followed by addition of water for extraction with ethyl acetate. The organic phase was washed in saturated aqueous sodium and dried over magnesium sulfate, and the solvent was distilled off under reduced pressure. The residue obtained was subjected to chromatography on a silica gel column, and from a fraction eluted with chloroform-methanol(98:2 v/v) was obtained 0.77 g of ethyl 4-[2-oxo-2-(3-pyridyl)ethyl]-α-methylcinnamate.

8) Ethyl 4-[2-oxo-2-(3-pyridyl)ethyl]-α-methylcinnamate (0.77 g) and ammonium formate (4.73 g) were stirred under heating at 150° C. for three hours.

After addition of water and extraction with chloroform, the organic phase was washed in saturated aqueous sodium solution and dried over anhydrous magnesium sulfate, and the solvent was distilled off under reduced pressure. The residue obtained was subjected to chromatography on a silica gel column, and from a fraction eluted with chloroform-methanol (95:5 v/v) was obtained 0.21 g of ethyl 4-[2-formamido-2-(3-pyridyl)ethyl]-α-methylcinnamate.

9) Ethyl 4-[2-formamido-2-(3-pyridyl)ethyl]-α-methylcinnamate (0.21 g) was stirred into 10 ml of a mixture solvent of ethanol and dioxane (1:1 v/v).

The reaction mixture was poured into saturated aqueous sodium hydrogencarbonate solution, which was then extracted with ethyl acetate. The organic phase was then washed in saturated aqueous sodium chloride and dried over magnesium sulfate, followed by distillation of the solvent under reduced pressure, to obtain 0.17 g of ethyl 4-[2-amino-2-(3-pyridyl)ethyl]-α-methylcinnamate.

10) To the solution of 0.17 g of ethyl 4-[2-amino-2-(3-pyridyl)ethyl]-α-methylcinnamate and 0.07 g of triethylamine in 5 ml of methylene chloride was added 0.14 g of chlorobenzene sulfonylchloride, and stirred overnight.

To the reaction mixture was added water, which was then extracted with ethyl acetate. The organic phase was then washed in saturated aqueous sodium chloride and dried over magnesium sulfate, followed by distillation of the solvent under reduced pressure. The residue obtained was subjected to chromatography on a silica gel column, and from a fraction eluted with chloroform-methanol(98:2 v/v) was obtained 0.16 g of ethyl 4-[2-(4-chlorobenzenesulfonamido-2-(3-pyridyl)ethyl]-α-methylcinnamate.

The spectrometric data thereof supports the structure of [42] as follows.

Chemical Formula 42

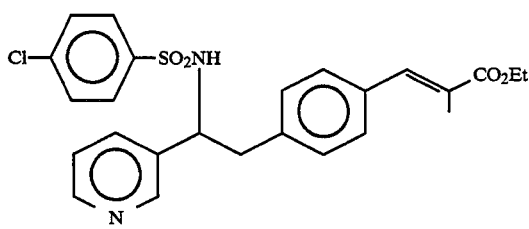

[42]

$^1$H NMR (CDCl$_3$-Methanol d$_4$) δ: 1.36(3H, t, J=7.3 Hz), 2.08(3H, br. s), 3.02(2H, d, J=7.3 Hz), 4.29(2H, q, J=7.3 Hz), 4.58(2H, t, J=7.3 Hz), 6.94–8.40(13H, m)

EXAMPLE 35

Ethyl 4-[2-(4-chlorobenzenesulfonamido-2-(3-pyridyl)ethyl]-α-methylcinnamate (120 rag) was dissolved in a mixed solvent of 10 ml of ethanol and dioxane (1:1 v/v) followed by addition of 5 ml of aqueous 2N sodium hydroxide solution, and stirred for 18 hours.

The solvent was distilled off under reduced pressure, and the resulting mixture was neutralized with 2N hydrogen chloride, and the crystalline deposited was filtered to obtain 82 mg of 4-[2-(4-chlorobenzenesulfonamido-2-(3-pyridyl)ethyl]-α-methylcinnamic acid.

The spectrometric data supports the structure of [43] as follows.

Chemical Formula 43

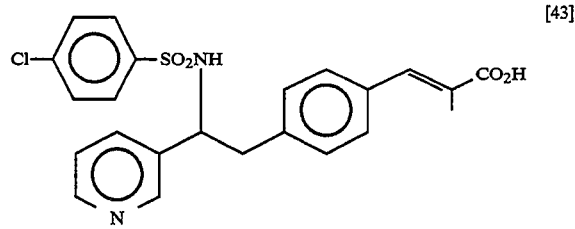

[43]

$^1$H NMR( DMSO d$_6$) δ: 1.98(3H, br. s), 2.90(2H, br. d, J=7.3 Hz), 4.52(1H, t, J=7.3 Hz), 6.90–8.40(13H, m)

EXAMPLE 3

1) Methyl toluirate (26.29 g ), N-bromosuccinimide (34.26 g) and benzoyl peroxide (0.22 g) were dissolved in 450 ml of carbon tetrachloride, and refluxed for two hours. The solvent in the filtrate was distilled off under reduced pressure to quantitatively obtain methyl 4-bromomethylbenzoate. The suspension of the methyl 4-bromomethylbenzoate, 11.40 g of potassium cyanide and 5.84 g of 18-crown-6 in 500 ml of acetonitrile was refluxed under heating for 24 hours.

The reaction mixture was filtered, and the filtrate was concentrated under reduced pressure followed by addition of water, which was then extracted with methylene chloride. The organic phase was washed in water, dried over anhydrous magnesium sulfate, and the solvent was distilled off under reduced pressure. The residue obtained was subjected to chromatography on a silica gel column, and from a fraction eluted with hexane-ethyl acetate (4:1 v/v) was obtained 7.14 g of methyl 4-cyanomethylbenzoate.

2) In nitrogen atmosphere, 11.92 g of methyl 4-cyanomethylbenzoate was dissolved in 300 ml of dry tetrahydrofuran, followed by dropwise addition of the solution of 136 ml of the 1.5M diisobutyl aluminium hydride in toluene at −78° C., and stirred at the same temperature for two hours.

After the temperature increase to 0° C., aqueous 2N sodium hydroxide solution was gradually added dropwise, for degradation of excess reagents. The property of the solution was made acidic with 2N hydrogen chloride, which was then extracted with ethyl acetate. The organic phase was washed in water, dried over anhydrous magnesium sulfate, and the solvent was distilled off under reduced pressure. The residue obtained was subjected to chromatography on a silica gel column, and from a fraction eluted with methanol-methylene chloride (5:95 v/v) was obtained 10.01 g of 4-cyanomethylbenzyl alcohol.

3) 4-Cyanomethylbenzyl alcohol (2.23 g), pyridium chlorochlomate (6.56 g) and molecular sieve 4A (10 g) in 120 ml of chloroform in suspension were stirred for 18 hours.

The reaction mixture was concentrated under reduced pressure, diluted with ether, dried over anhydrous magnesium sulfate, and filtered through a phlorizyl membrane. The solvent was distilled off under reduced pressure from the filtrate. The residue obtained was subjected to chromatography on a silica gel column, and from a fraction eluted with methanol-methylene chloride (3:97 v/v) was obtained 1.11 g of 4-cyanomethylbenzaldehyde.

4) 4-Cyanomethylbenzaldehyde (1.11 g), methyl ortho-formate (1.62 g) and amberlist 15(0.20 g) were stirred for 17 hours, and the reaction mixture was filtered, which was then subjected to repeated azeotropic process with carbon tetrachloride from the filtrate, to obtain 1.27 g of 4-cyanomethylbenzaldehyde dimethyl acetal.

5) In nitrogen atmosphere, the 15 ml of the solution of 0.40 g of diisopropylamine in dry tetrahydrofuran was cooled to −25° C., followed by dropwise addition of the solution of 1.6M n-butyl lithium in 2.54 ml of hexane, and stirred for 10 minutes. Furthermore, 0.63 g of the solution of 1.27 g of 4-cyanomethylbenzaldehyde dimethyl acetal in 15 ml of dry tetrahydrofuran was added dropwise, and stirred for 10 minutes at the same temperature.

Additionally, 3.24 g of hexamethylphosphoric triamide was added, followed by dropwise addition of the solution of picolyl chloride hydro chloride washed in saturated aqueous sodium hydrogencarbonate solution, followed by addition of 10 ml of ether, and dried over magnesium sulfate. Then, agitation was effected at room temperature for 24 hours.

To the reaction mixture was added saturated aqueous sodium chloride solution, followed by extraction with ethyl acetate and thorough washing in water, which was then dried over magnesium sulfate. The solvent was subsequently distilled off under reduced pressure. The obtained residue was subjected to chromatography on a silica gel column, and from a fraction eluted with methylene chloride, 0.21 g of 4-[ 1-cyano-2-(3-pyridyl-)ethyl]benzaldehyde dimethyl acetal was obtained.

6) An appropriate amount of Raney nickel was suspended in 5 ml of saturated ammonium methanol solution, followed by addition of 208 mg of 4-[1-cyano-2-(3-pyridyl)ethyl]benzaldehyde dimethyl acetal, and the resulting mixture was stirred in hydrogen atmosphere at 15 atm, for 10 hours.

The reaction mixture was filtered, and the filtrate was concentrated under reduced pressure. The obtained residue was subjected to chromatography on a silica gel column, and from a fraction eluted with aqueous ammonia-methanol-chloroform (1:10:100 v/v), 140 mg of 4-[1-amino-3-(3-pyridyl)-2-propyl]benzaldehyde dimethyl acetal was obtained.

7) 4-[1-Amino-3-(3-pyridyl)-2-propyl]benzaldehyde dimethyl acetal (3.06 g) and triethylamine (1.79 mg) were dissolved in 100 ml of methylene chloride followed by addition of 2.70 g of 4-chlorobenzenesulfonyl chloride, and stirred at room temperature for 24 hours. Then, the solvent was distilled off under reduced pressure, followed by addition of 50 ml of methanol and 24 ml of 6N hydrogen chloride and stirred for 80 minutes.

After stirring, neutralization was effected with aqueous 2N sodium hydroxide solution, followed by extraction with ethyl acetate. The organic phase was washed in saturated aqueous sodium chloride solution and dried over magnesium sulfate. The solvent was then distilled off under reduced pressure. The residue obtained was subjected to chromatography on a silica gel column, and from a fraction eluted with methanol-methylene chloride (5:95 v/v) was obtained 2.17 g of 4-[1-(4-chlorobenzenesulfonamido)-3-(3-pyridyl)-2-propyl]-benzaldehyde dimethyl acetal.

8) 4-[1-(4-Chlorobenzenesulfonamido)-3-(3-pyridyl)-2-propyl]benzaldehyde dimethyl acetal (2.17 g) and (carboethylidene)triphenylphosphorane (3.98 g) were dissolved in 100 ml of methylene chloride, and stirred for 15 hours.

The solvent was distilled off under reduced pressure, and the residue obtained was subjected to chromatography on a silica gel column. From a fraction eluted with methanol-methylene chloride (5:95 v/v) was obtained a mixture of a product and triphenylphosphine oxide.

The resulting mixture was dissolved in 50 ml of ethanol, followed by addition of 10 ml of aqueous 2N sodium hydroxide solution, and refluxed for 2.5 hours. The solvent was distilled off under reduced pressure from the reaction mixture, to which were added ethyl acetate and 2N sodium hydroxide. The aqueous phase was extracted with ethyl acetate after the separation of the aqueous phase.

The aqueous phase was neutralized with 6N hydrogen chloride, extracted with ethyl acetate, washed in aqueous sodium chloride solution, and dried over magnesium sulfate. Then, the solvent was distilled off under reduced pressure. The resulting crude product was tritiated with ether, to obtain 1.97 g of 4-[1-(4-chlorobenzenesulfonamido)-3-(3-pyridyl)-2-propyl]-α-methylcinnamic acid.

The spectrometric data supports the structure of [44] as follows.

Chemical Structure 44

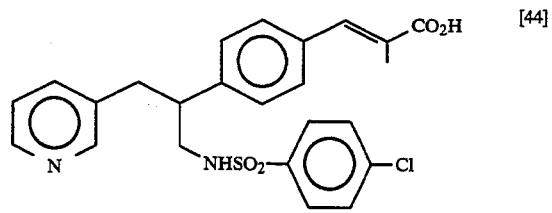

[44]

$^1$H NMR (CDCl$_3$=Methanol 9:1v/v) δ: 2.07(3H, br. s), 2.57–3.52(5H, m), 6.80–7.85(1H, m), 8.07–8.43(2H, m)

EXAMPLE 37

To 0.60 g of 4-[1-(4-chlorobenzenesulfonamido)-3-(3-pyridyl)-2-propyl]-α-methylcinnamic acid thionyl chloride and stirred for one hour. To the mixture was added 5 ml of ethanol at 0° C., and stirred for three hours, followed by dropwise addition of saturated aqueous sodium hydrogencarbonate and extraction with ethyl acetate and then further washing in saturated aqueous sodium chloride solution, and dried over magnesium sulfate to distill off the solvent. The residue obtained was subjected to chromatography on a silica gel column, and from a fraction eluted with methanol-methylene chloride (5:95 v/v) was obtained 0.49 g of ethyl 4-[1-(4-chlorobenzenesulfonamido)-3-(3-pyridyl)-2-propyl]-α-methylcinnamate.

The spectrometric data supports the structure of [44] as follows.

Chemical Formula 45

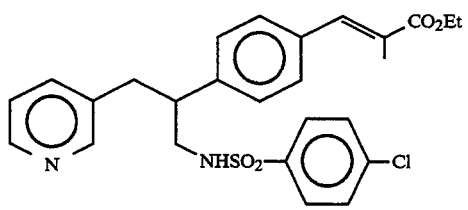

[45]

$^1$H NMR (CDCl$_3$) δ: 1.35(3H, t, J=7.0 Hz), 2.09(3H, d, J=5 Hz), 2.68–3.50(5H, m), 4.27(2H, q, J=7.0 Hz), 4.52–4.80(1H, m), 6.88–7.84(1H, m), 8.11–8.51(2H, m)

EXAMPLE 38

1) p-Bromobenzaldehyde (15.03 g), methyl ortho-formate (17.24 g) and amberlist 15(1.00 g) were stirred for 16 hours, and the reaction mixture was filtered. The filtrate was then subjected to azeotropic process with carbon tetrachloride, to obtain 18.58 g of 4-bromobenzaldehyde dimethyl acetal.

2) In argon atmosphere, the 18 ml of the solution of a Grignard reagent in tetrahydrofuran was prepared from 5.00 g of p-bromobenzaldehyde dimethyl acetal and 0.58 g of magnesium. After cooling to 0° C., 2.09 g of pyridine-3-aldehyde dissolved in 10 ml of dry tetrahydrofuran was added to the solution, and stirred for 20 hours.

To the reaction mixture was added saturated aqueous sodium chloride solution, followed by extraction with ethyl acetate, which was then dried over magnesium sulfate. Then, the solvent was distilled off under reduced pressure. The obtained residue was subjected to chromatography on a silica gel column, and from a fraction eluted with ethyl acetate, 2.16 g of 4-(hydroxy-3-pyridylmethyl)benzaldehyde dimethyl acetal was obtained.

3) 30.49 g of 4-(hydroxy-3-pyridylmethyl)benzaldehyde dimethyl acetal and 55.00 g of activated manganese dioxide were suspended in 800 ml of chloroform, and stirred at room temperature for 16 hours. The reaction mixture was filtered, and the solvent in the filtrate was distilled off under reduced pressure, to obtain 29.68 g of 4-nicotylbenzaldehyde dimethyl acetal.

4) In nitrogen atmosphere, 0.11 g of sodium was added to 30 ml of dry ethanol to produce ethoxide. Diethyl cyanomethyl phosphonate (0.83 g) dissolved in 10 ml of dry ethanol was added, followed by addition of 1.00 g of 4-nicotylbenzaldehyde dimethyl acetal, for reflux for 17 hours.

The solvent was distilled off, followed by addition of water for extraction with ethyl acetate, which was then washed in saturated aqueous sodium chloride solution. After drying over anhydrous magnesium sulfate, the solvent was distilled off. The residue obtained was subjected to chromatography on a silica gel column, and from a fraction eluted with ethyl acetate, 0.88 g of 4-[(E +Z)-2-cyano-1-(3-pyridyl)ethenyl)benzaldehyde dimethyl acetal was obtained.

5) An appropriate amount of Raney nickel was suspended in 30 ml of saturated ammonium methanol solution, followed by addition of 0.88 g of 4-[(E +Z)-2-cyano-1-(3-pyridyl)ethenyl)benzaldehyde dimethyl acetal, and stirred in hydrogen atmosphere at 15 atm. for 14 hours. The resulting mixture was filtered, and the solvent was then distilled off under reduced pressure.

The obtained residue was subjected to chromatography on a silica gel column, and from a fraction eluted with aqueous ammonia-methanol-chloroform (1:10:100 v/v), 0.31 g of 4-[3-amino-1-(3-pyridyl)-2-propyl]benzaldehyde dimethyl acetal was obtained.

6) To 4-[3-amino-1-(3-pyridyl)-2-propyl]benzaldehyde dimethyl acetal (0.31 g) and triethylamine (0.13 g) in 10 ml of methylene chloride in solution was added 0.27 g of p-chlorobenzene sulfonylchloride, and stirred for 20 hours. To the reaction mixture was added saturated aqueous sodium chloride solution, followed by extraction with methylene chloride and washing in 2N hydrogen chloride and saturated aqueous sodium chloride solution, which was then dried over magnesium sulfate. Then, the solvent was distilled off.

The residue was subjected to chromatography on a silica gel column, and from a fraction eluted with methanol-methylene chloride (5:95 v/v) was obtained a product. The product was dissolved in 6 ml of methanol, followed by addition of 1 ml of 6N hydrogen chloride, and stirred for one hour. The solvent was distilled off, followed by addition of water and extraction with methylene chloride. The organic phase was washed in saturated aqueous sodium chloride solution and dried over anhydrous magnesium sulfate, for evaporation of the solvent under reduced pressure. Subsequently, 0.22 g of 4-[3-(4-chlorobenzenesulfonamido)-1-(3-pyridyl)-2-propyl]benzaldehyde was obtained.

7) The solution of 220 mg of 4-[3-(4-chlorobenzenesulfonamido)-1-(3-pyridyl)-2-propyl]benzaldehyde and 420 mg of (carboethoxyethylidene)triphenylphosphorane in 20 ml of chloroform in solution was stirred under heating for five hours. To the reaction mixture was added water, followed by separation of the organic phase, which was then extracted with methylene chloride. After washing in saturated aqueous sodium chloride solution, the product was then dried over magnesium sulfate, followed by evaporation of the solvent. The residue obtained was subjected to preparative TLC on silica gel, which was developed with methylene chloride three times, to obtain 186 mg of ethyl 4-[3-(4-chlorobenzenesulfonamido)-1-(3-pyridyl)-2-propyl]-α-methylcinnamate. The spectrometric data thereof supports the structure of [46] as follows.

Chemical Formula 46

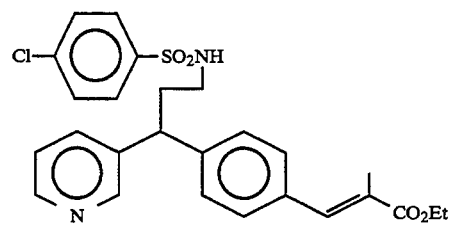

[46]

$^1$H NMR (CDCl$_3$) δ: 1.35(3H, t, J=7.0 Hz), 2.09(3H, d, J=1.5 Hz), 2.68–3.50(5H, m), 4.27(2H, q, J=7.0 Hz), 4.52–4.80(1H, m), 6.88–7.84(1H, m), 8.11–8.51(2H, m)

EXAMPLE 39

Ethyl 4-[3-(4-chlorobenzenesulfonamido)-1-(3-pyridyl)-2-propyl]-α-methylcinnamate was hydrolyzed in a similar manner to produce 4-[3-(4-chlorobenzenesulfonamido)-1-(3-pyridyl)-2-propyl]-α-methylcinnamic acid, which spectrometric data supports the structure of [47] as follows.

Chemical Formula 47

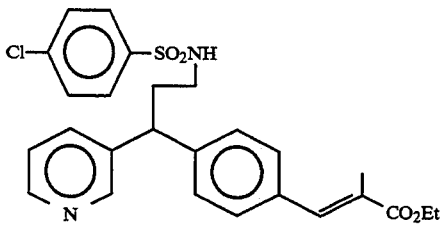

[47]

¹H NMR (CDCl₃-Methanol d₄) δ: 2.07(3H, br. s), 2.57–3.52(5H, m), 6.80–7.85(1H, m), 8.07–8.43(2H, m)

EXAMPLE 40

1) 4-[(E+Z)-2-cyano-1-(3-pyridyl)ethenyl]benzaldehyde dimethyl acetal (11.35 g) and sodium borohydride (11.35 g) were suspended in 200 ml of ethanol, and stirred for 24 hours.

The solvent was distilled off, followed by addition of water and extraction with ethyl acetate, and subsequently washed in saturated aqueous sodium chloride and dried over magnesium sulfate. Then, the solvent was distilled off under reduced pressure. The residue obtained was subjected to chromatography on a silica gel column, and from a fraction eluted with methanol-methylene chloride (3:97 v/v), 5.49 g of 4-[2-cyano-1-(3-pyridyl)ethyl]benzaldehyde dimethyl acetal was obtained.

2) 4-[2-Cyano-1-(3-pyridyl)ethyl]benzaldehyde dimethyl acetal (1.01 g) was dissolved in 50 ml of toluene, cooled to −78° C., followed by addition of the 7.15 ml of the solution of 1.5M diisobutyl aluminium hydride in toluene. Then, the temperature was gradually increased to room temperature before stirring for six hours. Aqueous 2N sodium hydroxide solution was dropwise added, and the organic phase was separated which was then extracted with ethyl acetate from aqueous phase.

The residue obtained was subjected to chromatography on a silica gel column, and from a fraction eluted with methanol-methylene chloride (3:97 v/v), 0.60 g of 4-[2-formyl-1-(3-pyridyl)ethyl]benzaldehyde dimethyl acetal was obtained.

3) In nitrogen atmosphere, 0.79 g of 4-[2-formyl-1-(3-pyridyl)ethyl]benzaldehyde dimethyl acetal was dissolved in 30 ml of dry ether, cooled to 0° C., followed by addition of 0.11 g of aluminium hydride, and stirred for 24 hours. After addition of ethyl acetate before stirring, aqueous solution of Russel salt was dropwise added to separate the organic phase which was then extracted wit ethyl acetate from the aqueous phase.

The organic phases combined were washed in saturated aqueous sodium chloride solution, dried over magnesium sulfate, and the solvent was distilled off under reduced pressure. The residue obtained was subjected to chromatography on a silica gel column, and from a fraction eluted with methanol-methylene chloride (5:95 v/v), 0.51 g of 4-[3-hydroxy-1-(3-pyridyl)-propyl]benzaldehyde dimethyl acetal was obtained.

4-[3-Hydroxy-1-(3-pyridyl)propyl]benzaldehyde dimethyl acetal (0.51 g) was dissolved in 10 ml of methanol, followed by addition of 5 ml of 6N hydrogen chloride, and stirred for 20 hours. The solvent was distilled off under reduced pressure, followed by neutralization with aqueous 2N sodium hydroxide solution, which was then extracted with methylene chloride. The organic phase was washed in saturated aqueous sodium chloride solution, dried over anhydrous magnesium sulfate, and the solvent was distilled off under reduced pressure, to obtain 0.43 g of 4-[3-hydroxy-1-(3-pyridyl)propyl]benzaldehyde.

5) The solution of 0.43 g of 4-[3-hydroxy-1-(3-pyridyl)propyl]benzaldehyde and 1.24 g of (carboethoxyethylidene)triphenylphosphorane in 30 ml of chloroform was stirred for 22 hours. The solvent was distilled off under reduced pressure, and the obtained residue was subjected to chromatography on a silica gel column, and from a fraction eluted with ethyl acetate, 0.28 g of ethyl 4-[3-hydroxy-1-(3-pyridyl)propyl]-α-methylcinnamate.

6) Ethyl 4-[3-Hydroxy-1-(3-pyridyl)propyl]-α-methylcinnamate (0.41 g) was dissolved in 10 ml of acetone solution, which was then cooled to 0° C., followed by dropwise addition of 2.67M Jones Reagent, and stirred for 10 minutes. Then, water was added and extraction with ethyl acetate was effected. The aqueous phase was extracted with saturated aqueous sodium hydrogencarbonate solution from the organic phase. After the aqueous phase was acidified with 2N hydrogen chloride, the organic phase was extracted with ethyl acetate.

The organic phase was washed in saturated aqueous sodium chloride solution and dried over magnesium sulfate. The solvent was then distilled off under reduced pressure, to obtain 0.12 g of ethyl 4-[2-carboxy-1-(3-pyridyl)ethyl]-α-methylcinnamate.

7) Ethyl 4-[2-Carboxy-1-(3-pyridyl)ethyl]-α-methylcinnamate (89 mg), diphenylphosphorylamide (133 mg) and triethylamine (53 mg) were dissolved in a mixed solvent of 1 ml of t-butanol and 1 ml of N,N-dimethylformamide, and heated to 80 ° C. and stirred for 12 hours.

After addition of water, extraction with ethyl acetate and washing in saturated aqueous sodium chloride solution, drying over anhydrous magnesium sulfate was effected, and the solvent was subsequently distilled off under reduced pressure. The obtained residue was subjected to preparative TLC on a silica gel column which was then developed with methanol-methylene chloride (3:97 v/v), to obtain 13.6 mg of ethyl 4-[2-(t-butyloxycarbonylamido)-1-(3-pyridyl)ethyl]-α-methylcinnamate.

8) Ethyl 4-[2-(t-butyloxycarbonylamido)-1-(3-pyridyl)ethyl]-α-methylcinnamate (13.6 mg) was dissolved in 1 ml of methylene chloride and 1 ml of trifluoroacetic acid, and stirred at 60° C. for one hour. The reaction mixture was poured into water followed by adjustment to alkalinity with 2N sodium hydroxide, which was then extracted with ethyl acetate. The organic phase was washed in saturated aqueous sodium chloride, dried over magnesium sulfate. Then, the solvent was distilled off under reduced pressure to obtain 10.3 mg of ethyl 4-[2-amino-1-(3-pyridyl)ethyl]-α-methylcinnamate.

9) Ethyl 4-[2-amino-1-(3-pyridyl)ethyl]-α-methylcinnamate (10.3 mg) and triethylamine (40 mg) were dissolved in 2 ml of methylene chloride, followed by addition of 20 mg of p-chlorobenzene sulfonylchloride, and stirred at room temperature for 12 hours. To the reaction mixture was added water, and the organic phase was separated which was then extracted methylene chloride from aqueous phase.

The organic phase was washed in saturated aqueous sodium chloride solution and dried over magnesium sulfate, to distill off the solvent. The residue obtained was subjected to preparative TLC on silica gel, which was developed with methanol-methylene chloride (5:95 v/v), to obtain 12.3 mg of ethyl 4-[2-(4-chlorobenzenesulfonamido)-1-(3-pyridyl)ethyl]-α-methylcinnamate. The spectrometric data thereof supports the structure of [48] as follows.

Chemical Formula 48

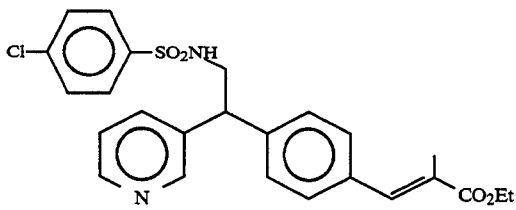

$^1$H NMR (CDCl$_3$) δ: 1.35(3H, t, J=7.2 Hz), 2.09(3H, d, J=1.3 Hz), 3.61(2H, dd, J=7.0, 7.8 Hz), 4.18(2H, t, J=7.8 Hz), 4.27(2H, q, J=7.2 Hz), 4.81(1H, t, J=7.0 Hz), 7.05–7.95(11H, m), 8.35–8.65(2H, m)

EXAMPLE 41

Ethyl 4-[2-(4-chlorobenzenesulfonamido)-1-(3-pyridyl)ethyl]-α-methylcinnamate (6.8 mg) was dissolved in 1 ml of methanol, followed by addition of 0.2 ml of aqueous 2N sodium hydroxide solution, and refluxed for 18 hours. The solvent was distilled off under reduced pressure. The crystalline deposited through neutralization of the resulting mixture with 2N hydrogen chloride was filtered, to obtain 6.4 mg of 4-[2-(4-chlorobenzenesulfonamido)-1-(3-pyridyl)ethyl]-α-methylcinnamic acid. The spectrometric data thereof supports the structural formula of [49] as follows.

Chemical Formula 49

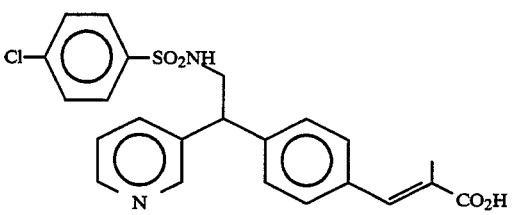

$^1$H NMR (DMSO d$_6$) δ: 1.98(3H, br. s), 7.20–8.60(13H, m)

EXAMPLE 42

1) In nitrogen atmosphere, sodium hydroxide (1.23 g) was washed in hexane and suspended in 100 ml of dry tetrahydrofuran, to which was dropwise added, at 0° C., 50 ml of the solution of dry tetrahydrofuran containing 4.83 g of the 2-pyrrolyl 3-pyridyl ketone synthesized according to the known method (Journal of Medicinal Chemistry, 26, 1164(1983)) over 15 minutes, and stirred for 30 minutes, followed by dropwise addition of 4.38 g of methyl iodide dissolved in 10 ml of dry tetrahydrofuran. After further addition of 50 ml of dimethyl sulfoxide, the mixture was stirred for 12 hours.

To the reaction mixture was added water, and the organic phase was separated which was then extracted methylene chloride from aqueous phase. The organic phases combined were washed in saturated aqueous sodium chloride solution and dried over magnesium sulfate, to distill off the solvent. The residue obtained was subjected to chromatography on a silica gel column and from a fraction eluted with methanol-methylene chloride (3:97 v/v) was obtained 4.07 g of 1-methyl-2-pyrrolyl 3-pyridyl ketone.

2) In nitrogen atmosphere, 0.66 g of sodium hydride was washed in hexane, and suspended in 40 ml of N,N-dimethylformamide, followed by dropwise addition of 2.94 g of dimethyl cyanomethyl phosphonate dissolved in 10 ml of N,N-dimethylformamide, and further followed by dropwise addition of 2.81 g of 1-methyl-2-pyrrolyl 3-pyridyl ketone dissolved in 5 ml of dimethylformamide, and stirred at 60° C. for 24 hours.

To the reaction mixture was added water for extraction with ethyl acetate, followed by washing in saturated aqueous sodium chloride, and dried over anhydrous magnesium sulfate. Then, the solvent was distilled off to obtain 3.10 g of (E+Z)-3-(1-methyl-2-pyrrolyl)-3-(3-pyridyl)acrylonitrile.

3) (E+Z)-3-(1-methyl-2-pyrrolyl)-3-(3-pyridyl)acrylonitrile (2.23 g) and sodium borohydride (4.46 g) were suspended in 50 ml of ethanol, and refluxed for 12 hours. The reaction mixture was concentrated under reduced pressure, followed by addition of water and extraction with ethyl acetate, and washed in saturated aqueous sodium chloride solution and dried over anhydrous magnesium sulfate, to distill off the solvent. The residue obtained was subjected to chromatography on a silica gel column. From a fraction eluted with methanol-methylene chloride (5:95 v/v) was obtained 1.06 g of 3-(1-methyl-2-pyrrolyl)-3-(3-pyridyl)propionitrile.

4) An appropriate amount of Raney nickel was suspended in 15 ml of saturated ammonium methanol solution, followed by addition of 0.71 g of 3-(1-methyl-2-pyrrolyl)-3-(3-pyridyl)propionitrile, and stirred in hydrogen atmosphere at 15 atm. for 14 hours. The reaction mixture was filtered, while the solvent was distilled off under reduced pressure.

The residue obtained was subjected to chromatography on a silica gel column, which was then eluted with aqueous ammonia-methanol-chloroform (1:10:100 v/v). From such an eluted fraction was obtained 0.59 g of 3-(1-methyl-2-pyrrolyl)-3-(3-pyridyl)propylamine.

5) 3-(1-Methyl-2-pyrrolyl)-3-(3-pyridyl)propylamine (0.59 g) and triethylamine (0.31 g) were dissolved in 20 ml of methylene chloride, followed by addition of 0.64 g of p-chlorobenzene sulfonylchloride, and stirred at room temperature for 18 hours. To the reaction mixture was added 2N hydrogen chloride, and the organic phase was separated, which was then extracted with methylene chloride from the aqueous phase. After washing in saturated aqueous sodium hydrogencarbonate and in aqueous saturated sodium chloride solution and drying over magnesium sulfate, the solvent was distilled off to obtain 0.96 g of N-[3-(1-methyl-2-pyrrolyl)-3-(3-pyridyl)propyl]-4-chlorobenzenesulfonamide.

6) N,N-dimethylformamide (5 ml) was cooled to 0° C., followed by addition of 0.25 ml of phosphorous oxychloride, and stirred for five minutes. N-[3-(1-Methyl-2-pyrrolyl)-3(3-pyridyl)-4-chlorobenzenesulfonamide (0.87 g) dissolved in N,N-dimethylformamide (1 ml) was added, for agitation at room temperature for 24 hours To the reaction mixture was added aqueous 2N sodium hydroxide solution for hydrolysis, followed by addition of aqueous sodium chloride solution, which was then extracted with ethyl acetate. The organic phase was washed in aqueous sodium chloride solution and dried over magnesium sulfate, and the solvent was distilled off under reduced pressure. The residue obtained was subjected to chromatography on a silica gel column, and from a fraction eluted with ethyl acetate was obtained 0.62 g of 4-[3-(4-chlorobenzenesulfonamido)-1-(3-pyridyl)propyl]-1-methylpyrrolyl-2-carbaldehyde.

7) 4-[3-(4-Chlorobenzenesulfonamido)-1-(3-pyridyl)propyl]-1-methylpyrrolyl-2-carbaldehyde (0.62 g) and (carboethoxyethylidene) triphenylphosphorane (2.58 g) were added, and stirred at room temperature for 16 hours, followed by reflux for another seven hours. The solvent was distilled off, and the residue obtained was subjected to chromatography and the fraction eluted with ethyl acetate was obtained a mixture of triphenylphosphine oxide and an objective product.

The mixture was dissolved in 15 ml of ethanol, followed by addition of aqueous 2N sodium hydroxide solution, and refluxed for 20 hours. The solvent was distilled off, followed by addition of methylene chloride, which was then extracted with aqueous 2N sodium hydroxide solution. The solvent was distilled off under reduced pressure, followed by neutralization with aqueous 2N hydrogen chloride, which was then extracted with methylene chloride followed by washing in saturated aqueous sodium chloride solution and drying over magnesium sulfate. Subsequently, the solvent was distilled off under reduced pressure, to obtain 0.61 g of 3-{4-[3-(4-chlorobenzenesulfonamido)-1-(3-pyridyl)propyl]-1-methylpyrrol-2-yl}-2-methylacrylic acid. The spectrometric data supports the structure of [50] as follows.

Chemical Formula 50

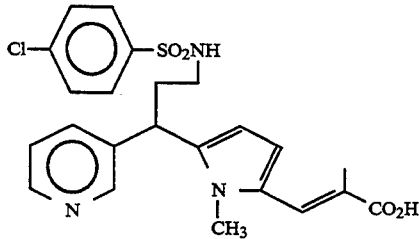

[50]

$^1$H NMR (CDCl$_3$) δ: 2.11(3H, br. s), 2.00–2.51(2H, m), 2.67–3.15(2H, m), 3.33(3H, s), 4.00–4.38(1H, m), 6.22(1H, d, J=3.8 Hz), 6.31–6.65(1H, m), 6.56(1H, d, J=3.8 Hz), 7.10–7.95(7H, m), 8.10–8.90(2H, m)

EXAMPLE 43

To the solution of 3-{4-[3-(4-chlorobenzenesulfonamido)-1-(3-pyridyl)propyl]-1-methylpyrrol-2-yl}-2-methylacrylic acid (0.53 g) in 5 ml of methylene chloride was added 1.0 ml of thionyl chloride, and stirred for 1.5 hours, followed by evaporation under reduced pressure. Twenty milliliters of methylene chloride and 2 ml of ethanol were added followed by addition of 1.0 ml of triethylamine at 0° C., and stirred for 30 minutes. 2N hydrogen chloride was added followed by separation of the organic phase, which was extracted with methylene chloride.

The organic phases combined were washed in saturated aqueous sodium hydrogencarbonate solution and then in saturated aqueous sodium chloride solution, and dried over magnesium sulfate, to distill off the solvent under reduced pressure. The residue obtained was subjected to chromatography on a silica gel column, and from a fraction eluted with methanol-methylene chloride (5:95 v/v) was obtained 0.30 g of ethyl 3-{4-[3-(4-chlorobenzenesulfonamido)-1-(3-pyridyl)propyl]-1-methylpyrrol-2-yl}-2-methylacrylate. The spectrometric data supports the structure of [51] as follows.

Chemical Formula 51

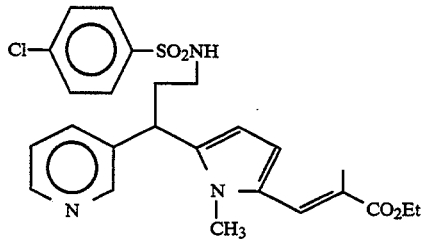

[51]

$^1$H NMR (CDCl$_3$) δ: 1.30(3H, t, J=7.0 Hz), 2.11(3H, br. s), 2.22(2H, dt, J=7.0, 7.0 Hz), 2.98(2H, dt, J=7.0, 7.0 Hz), 3.27(3H, s), 4.09(1H, t, J=7.0 Hz), 4.19(1H, t, J=7.0 Hz), 5.98(1H, t, J=7.0 Hz), 6.14(1H, d, J=4.5 Hz), 6.46(1H, d, J=4.5 Hz), 7.00–7.85(6H, m), 8.27–8.52(2H, m)

Test Example 1

Platelet aggregation inhibiting activity

A blood sample was collected from human fore arm using a syringe containing 3.8% sodium citrate solution (1/10 volume of the blood to be collected) and centrifuged to obtain platelet rich plasma (PRP; 3 × 10$^5$ platelets/μl).

Platelet aggregation was measured using an aggregometer (Hematracer VI, Niko Bioscience Co., Ltd.) by putting 200 μl of the thus prepared PRP and 23.75 μl of physiological saline in a cuvette, setting the cuvette into the aggregometer and incubating the contents at 37° C. for 2 minutes, adding 1.25 μl dimethyl sulfoxide (DMSO) solution of each of the N-(3-pyridylalkyl)sulfonamide derivatives obtained in Examples 1, 3, 4, 6 and 8 and incubating for 3 minutes, and then adding U-46619 (Cayman Chemical Co., Inc.) which is a stable PGG$_2$/H$_2$ derivative having a strong platelet aggregation causing activity. Table 1 shows concentrations (IC$_{50}$) of the inventive derivatives to inhibit 50% of platelet aggregation caused by 320 nM of the U-46619.

TABLE 1

| Example | Structure | Inhibitory effect against platelet aggregation caused by U-46619 (IC$_{50}$;M) |
|---|---|---|
| 1 | [9] | 9.6 × 10$^{-5}$ |
| 4 | [12] | 5.1 × 10$^{-5}$ |
| 5 | [13] | 1.6 × 10$^{-5}$ |
| 7 | [15] | 3.0 × 10$^{-5}$ |
| 9 | [17] | 5.1 × 10$^{-6}$ |

As is evident from the results shown in Table 1, each of the N-(3-pyridylalkyl)sulfonamide derivatives obtained in Examples 1, 4, 5, 7 and 9 is possessed of markedly high platelet aggregation inhibiting activity. It was confirmed also that other N-(3-pyridylalkyl)sulfonamide derivatives of the present invention obtained in Examples 2, 6 and 8 have similar activities. In this instance, the term "IC$_{50}$"as used herein means concentration of the N-(3-pyridylalkyl)sulfonamide derivative of the present invention required to inhibit 50% of the platelet agglutination when platelet aggregation without introducing the inventive derivative was defined as 100%.

Test Example 2

Thromboxane synthetase inhibiting activity

A blood sample was collected from human fore arm using a syringe containing 3.8% sodium citrate solution (1/10 volume of the blood to be collected) and centrifuged to obtain platelet rich plasma (PRP; $3 \times 10^5$ platelets/$\mu$l).

A 200 $\mu$l portion of the thus prepared PRP and 23.75 $\mu$l of physiological saline were put in a cuvette, the cuvette was set into the aforementioned aggregometer and the contents in the cuvette were incubated at 37° C. for 2 minutes. Thereafter, 1.25 $\mu$l dimethyl sulfoxide (DMSO) solution of each of the N-(3-pyridylalkyl)sulfonamide derivatives obtained in Examples 1, 3 and 7 was put in the cuvette and incubated for 3 minutes, followed by the addition of 20 U/ml solution of thrombin to cause platelet aggregation. A portion of the supernatant after aggregation reaction was mixed with diethyl ether/methanol/0.2M citric acid (30:4:1 ), and the thus formed thromboxane A2 was extracted and its quantity was analyzed by RIA using a kit of Amersham. The results are shown in Table 2.

TABLE 2

| Example | Structure | Inhibition of thromboxane $A_2$ synthesis ($IC_{50}$;M) |
|---|---|---|
| 1 | [9] | $3.7 \times 10^{-8}$ |
| 4 | [12] | $3.3 \times 10^{-8}$ |
| 8 | [16] | $4.3 \times 10^{-6}$ |

As is evident from the results shown in Table 2, each of the N-(3-pyridylalkyl)sulfonamide derivatives obtained in Examples 1, 3 and 7 is possessed of excellent thromboxane synthetase inhibiting activity. It was confirmed also that other derivatives of the present invention obtained in Examples 2, 5, 6, 7 and 9 have similar excellent activities.

Test Example 3

Competitive activity against $TXA_2.PGH_2$

In vitro competitive activity ($IC_{50}$) of the derivative of the present invention against $TXA_2.PGH_2$ was measured as follows.

Sections of tracheae excised from Hartley guinea pig males of 300 to 500 g in weight were suspended with a load of 0.3 g in Tyrode solution (30° C.) contained in a Magnus vessel which was aerated with a mixed gas system of 95% oxygen and 5% carbon dioxide. After about 1 hour of stabilization, U-46619 (a $TXA_2.PGH_2$ analog, manufactured by Cayman Chemical Co., Inc.) was added to the solution in a concentration of $10^{-7}$M. Thereafter, effect of the addition of the inventive N-(3-pyridylalkyl)sulfonamide derivative obtained in Example 4 on the tracheal smooth muscle contraction caused by the U-46619 was measured and the $IC_{50}$ value was calculated.

TABLE 3

| Example | Structure | Competitive activity against U-46619 ($IC_{50}$;M) |
|---|---|---|
| 5 | [13] | $6.7 \times 10^{-6}$ |

As is evident from the result shown in Table 3, the inventive derivative synthesized in Examples 4 is possessed of excellent in vitro competitive activity against $TXA_2.PGH_2$. It was confirmed also that other derivatives of the present invention obtained in Examples 1, 2, 4, 6, 7, 8 and 9 have similar excellent activities.

Test Examples 4

Platelet aggregation inhibiting activity

A blood sample was taken from carotid artery of a guinea pig using a syringe containing 3.8% sodium citrate solution (1/10 volume of the blood to be collected). The blood was centrifuged to obtain platelet riched plasma (PRP: number of platelets, $3 \times 10^5/\mu$l).

Two hundred microliters of the PRP and 23.75 $\mu$l of physiological saline were placed in a cuvette, which was then set in an aggregometer, followed by heating at 37° C. for two minutes, and then followed by addition of 1.25 $\mu$l of the solution of an N-(3-pyridylalkyl)sulfonamide derivative of the present invention in ethanol, for 3-min incubation. Then, U-46619, one of stable $PGG_2/H_2$ derivatives, having strong action inducing platelet aggregation, was added, so that platelet aggregation was measured by an aggregometer [Hematracer VI: manufactured by NIKO Bioscience, K.K.]. The concentration of 50% inhibition of platelet aggregation, induced by U-46619 (320 nM), is shown in Table 4.

As is shown in Table 4, the N-(3-pyridylalkyl)sulfonamide derivative of the present invention showed distinctive anti-platelet aggregation activity. It is confirmed that other N-(3-pyridylalkyl)sulfonamide derivatives of the present invention, obtained in Examples 10, 12, 14, 16, 18, 20, 22, 25, 28, 30 and 32, have similar activities.

TABLE 4

| Example No. | Platelet aggregation activity | |
|---|---|---|
| | Structural Formula | $IC_{50}$ (M) |
| 11 | [19] | $1.9 \times 10^{-6}$ |
| 13 | [21] | $8.4 \times 10^{-7}$ |
| 15 | [23] | $1.1 \times 10^{-6}$ |
| 17 | [25] | $1.8 \times 10^{-6}$ |
| 19 | [27] | $4.2 \times 10^{-6}$ |
| 21 | [29] | $6.8 \times 10^{-7}$ |
| 23 | [31] | $3.6 \times 10^{-7}$ |
| 24 | [32] | $4.0 \times 10^{-5}$ |
| 26 | [34] | $6.0 \times 10^{-5}$ |
| 27 | [35] | $5.2 \times 10^{-5}$ |
| 29 | [37] | $2.0 \times 10^{-6}$ |
| 31 | [39] | $1.5 \times 10^{-5}$ |
| 33 | [41] | $1.7 \times 10^{-5}$ |

Test Example 5

Thromboxane synthetase inhibiting activity

Arachidonic acid (10 nM) was added to 250 $\mu$g of microsome of sheep seminal vesicle gland, commercially available from Hilran Biochemical, Co. Ltd., Israel, Lot SM36, which was then reacted at room temperature for 90 seconds to prepare $PGH_2$.

Commercially available human platelet microsomal fraction (200 $\mu$g) as a source for thromboxane synthetase was mixed with the $PGH_2$ solution prepared in the same manner as for samples, and reacted together at room temperature for 60 seconds. Diethyl ether/methanol/0.2M citric acid (30:4:1) was added to extract thromboxane $A_2$ generated and its quantity was then analyzed by RIA using a kit manufactured by NEN, Co. LTd.

The results are shown in Table 5.

TABLE 5

Inhibition of thromboxane synthetase

| Example No. | Structure | IC$_{50}$ (M) |
|---|---|---|
| 11 | [9] | $2.1 \times 10^{-5}$ |
| 13 | [21] | $8.9 \times 10^{-6}$ |
| 15 | [23] | $3.6 \times 10^{-5}$ |
| 17 | [25] | $3.0 \times 10^{-5}$ |
| 19 | [27] | $1.0 \times 10^{-6}$ |
| 21 | [29] | $2.2 \times 10^{-6}$ |
| 23 | [31] | $5.1 \times 10^{-6}$ |
| 24 | [32] | $2.2 \times 10^{-6}$ |
| 26 | [34] | $2.4 \times 10^{-6}$ |
| 27 | [35] | $2.8 \times 10^{-5}$ |
| 29 | [37] | $1.5 \times 10^{-6}$ |
| 31 | [39] | $9.4 \times 10^{-7}$ |
| 33 | [41] | $3.0 \times 10^{-8}$ |

Test Examples 6

Platelet aggregation inhibiting activity

A blood sample was collected from human fore arm using a syringe containing 3.8% sodium citrate solution (1/10 volume of the blood to be collected) and centrifuged to obtain platelet rich plasma (PRP; $3 \times 10^5$ platelets/μl).

Platelet aggregation was measured using an aggregometer (Hematracer VI, Niko Bioscience Co., Ltd.) by putting 200 μof the thus prepared PRP and 23.75 μl of physiological saline in a cuvette, setting the cuvette into the aggregometer and incubating the contents at 37° C. for 2 minutes, adding 1.25 μl dimethyl sulfoxide (DMSO) solution of each of the N-(3-pyridylalkyl)sulfonamide derivatives obtained in Examples 35, 36, 37 and 42 and incubating for 3 minutes, and then adding U-46619 (Cayman Chemical Co., Inc.) which is a stable PGG$_2$/H$_2$ derivative having a strong platelet aggregation causing activity. Table 6 shows concentrations (IC$_{50}$) of the inventive derivatives to inhibit 50% of platelet aggregation caused by 320 nM of the U-46619.

TABLE 6

| Example | Structure | Inhibitory effect against platelet aggregation caused by U-46619 (IC$_{50}$;M) |
|---|---|---|
| 35 | [43] | $4.8 \times 10^{-5}$ |
| 36 | [44] | $7.1 \times 10^{-5}$ |
| 37 | [45] | $6.6 \times 10^{-5}$ |
| 42 | [50] | $4.3 \times 10^{-5}$ |

As is evident from the results shown in Table 6, each of the N-(3-pyridylalkyl)sulfonamide derivatives obtained in Examples 35, 36, 37 and 42 is possessed of markedly high platelet aggregation inhibiting activity. It was confirmed also that other N-(3-pyridylalkyl)sulfonamide derivatives of the present invention obtained in Examples 33-43 have similar activities. In this instance, the term "IC$_{50}$" as used herein means concentration of the N-(3-pyridylalkyl)sulfonamide derivative of the present invention required to inhibit 50% of the platelet aggregation when platelet aggregation without introducing the inventive derivative was defined as 100%.

Test Example 7

Thromboxane synthetase inhibiting activity

A blood sample was collected from human fore arm using a syringe containing 3.8% sodium citrate solution (1/10 volume of the blood to be collected) and centrifuged to obtain platelet rich plasma (PRP; $3 \times 10^5$ platelets/μl).

A 200 μl portion of the thus prepared PRP and 23.75 μl of physiological saline were put in a cuvette, the cuvette was set into the aforementioned aggregometer and the contents in the cuvette were incubated at 37° C. for 2 minutes. Thereafter, 1.25 μl dimethyl sulfoxide (DMSO) solution of each of the N-(3-pyridylalkyl)sulfonamide derivatives obtained in Examples 36, 37, 38 and 40 was put in the cuvette and incubated for 3 minutes, followed by the addition of 20 U/ml solution of thrombin to cause platelet aggregation. A portion of the supernatant after aggregation reaction was mixed with diethyl ether/methanol/0.2M citric acid (30:4:1), and the thus formed thromboxane A$_2$ was extracted and its quantity was analyzed by RIA using a kit of Amersham. The results are shown in Table 7.

TABLE 7

| Example | Structure | Inhibition of thromboxane A$_2$ synthesis (IC$_{50}$;M) |
|---|---|---|
| 36 | [44] | $8.3 \times 10^{-6}$ |
| 37 | [45] | $8.9 \times 10^{-6}$ |
| 38 | [46] | $1.4 \times 10^{-6}$ |
| 40 | [48] | $1.5 \times 10^{-6}$ |

As is evident from the results shown in Table 7, each of the N-(3-pyridylalkyl)sulfonamide derivatives obtained in Examples 36, 37, 38 and 40 is possessed of excellent thromboxane synthetase inhibiting activity. It was confirmed also that other derivatives of the present invention obtained in Examples 34-43 have similar excellent activities.

Test Examples 8

Competitive activity against TXA$_2$.PGH$_2$

In vitro competitive activity (IC$_{50}$) of the derivative of the present invention against TXA$_2$·PGH$_2$ was measured as follows.

Sections of tracheae excised from Hartley guinea pig males of 300 to 500 g in weight were suspended with a load of 0.3 g in Tyrode solution (30° C.) contained in a Magnus vessel which was aerated with a mixed gas system of 95% oxygen and 5% carbon dioxide. After about 1 hour of stabilization, U-46619 (a TXA$_2$·PGH$_2$ analog, manufactured by Cayman Chemical Co., Inc.) was added to the solution in a concentration of $10^{-7}$M. Thereafter, effect of the addition of the inventive N-(3-pyridylalkyl)sulfonamide derivative obtained in Example 4 on the tracheal smooth muscle contraction caused by the U-46619 was measured and the IC$_{50}$ value was calculated.

TABLE 8

| Example | Structure | Competitive activity against U-46619 (IC$_{50}$;M) |
|---|---|---|
| 37 | [45] | $8.8 \times 10^{-8}$ |

As is evident from the result shown in Table 8, the inventive derivative synthesized in Example 37 is possessed of excellent in vitro competitive activity against TXA2·PGH$_2$. It was confirmed also that other derivatives of the present invention obtained in Examples 34-43 have similar excellent activities. [Acute toxicity]

Using ICR male mice aged five weeks, experiments concerning acute toxicity via oral administration were carried out. All of the LD$_{50}$'s of N-(3-pyridylalkyl)sulfonamide derivatives of the present invention were 300 mg/kg or more, so that higher safety is thus confirmed.

We claim:

1. An N-(3-pyridylalkyl)sulfonamide derivative represented by the following formula, a pharmacologically acceptable salt thereof, or a pharmacologically acceptable hydrate thereof:

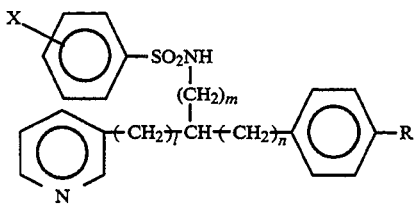

[A]

wherein X is hydrogen atom, a halogen atom, or a lower alkyl group; R is at least one group selected from the group consisting of —OR$^1$, —O(CH$_2$)$_a$COOR$^2$, —OCOOR$^3$, —CR$^4$=CR$^5$—COOR$^6$ and —(CH$_2$)$_b$—COOR$^7$, where each of R$^1$ to R$^7$ is independently hydrogen atom or a lower alkyl group and each of a and b is independently an integer of 0 to 4; and each of l, m and n is independently an integer of 0 to 4.

2. A pharmaceutical composition for the inhibition of thromboxane A$_2$ production, said composition comprising an effective amount of N-(3-pyridylalkyl) sulfonamide derivative of claim 1 to inhibit thromboxane A$_2$ production, a pharmacologically acceptable salt thereof, or a pharmacologically acceptable hydrate thereof and a pharmaceutically acceptable carrier therefor.

3. A pharmaceutical composition for use as a thromboxane A$_2$ antagonist, said composition comprising an effective amount of N-(3-pyridylalkyl)sulfonamide derivation of claim 1 for use as a thromboxane A$_2$ antagonist, a pharmacologically acceptable salt thereof, or a pharmacologically acceptable hydrate thereof and a pharmaceutically acceptable carrier therefor.

4. A pharmaceutical composition for use as a prostaglandin H$_2$ antagonist, said composition comprising an effective amount of N-(3-pyridylalkyl)sulfonamide derivative of claim 1 for use as a prostaglandin H$_2$ antagonist, a pharmacologically acceptable salt thereof, or a pharmacologically acceptable hydrate thereof and a pharmaceutically acceptable carrier therefor.

5. A pharmaceutical composition for use as an anti-thrombus agent, said composition comprising an effective amount of N-(3-pyridylalkyl)sulfonamide derivative of claim 1 for use as anti-thrombus agent, a pharmacologically acceptable salt thereof, or a pharmacologically acceptable hydrate thereof and a pharmaceutically acceptable carrier therefor.

6. A pharmaceutical composition for use as a thrombus-preventing agent, said composition comprising an effective amount of N-(3-pyridylalkyl)sulfonamide derivative of claim 1 for use as a thrombus-preventing agent, a pharmacologically acceptable salt thereof, or a pharmacologically acceptable hydrate thereof and a pharmaceutically acceptable carrier therefor.

7. A pharmaceutical composition for use as an anti-allergy agent, said composition comprising an effective amount of N-(3-pyridylalkyl)sulfonamide derivative of claim 1 for use as an anti-allergy agent, a pharmacologically acceptable salt thereof, or a pharmacologically acceptable hydrate thereof and a pharmaceutically acceptable carrier therefor.

* * * * *

UNITED STATES PATENT AND TRADEMARK OFFICE
CERTIFICATE OF CORRECTION

PATENT NO. : 5,374,641

DATED : December 20, 1994

INVENTOR(S) : Hiroyuki OHNISHI et al

It is certified that error appears in the above-indentified patent and that said Letters Patent is hereby corrected as shown below:

In Column 55, line 3, after "formula", insert -- [A] --.

Signed and Sealed this

Twenty-first Day of March, 1995

BRUCE LEHMAN

*Attest:*

*Attesting Officer*        *Commissioner of Patents and Trademarks*